(12) United States Patent
Fleer et al.

(10) Patent No.: US 10,204,443 B2
(45) Date of Patent: Feb. 12, 2019

(54) DENTAL IMAGE DISPLAY DEVICE, DENTAL SURGICAL OPERATION DEVICE, AND DENTAL IMAGE DISPLAY METHOD

(71) Applicant: J. Morita Manufacturing Corporation, Kyoto (JP)

(72) Inventors: Jürgen Richard Fleer, Dietzenbach (DE); Teruji Nakai, Kyoto (JP); Masakazu Suzuki, Kyoto (JP); Tomoyuki Sadakane, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 211 days.

(21) Appl. No.: 14/199,680

(22) Filed: Mar. 6, 2014

(65) Prior Publication Data

US 2014/0342301 A1 Nov. 20, 2014

(30) Foreign Application Priority Data

Mar. 6, 2013 (JP) ................... 2013-043707

(51) Int. Cl.
*A61B 5/00* (2006.01)
*G06T 15/08* (2011.01)
(Continued)

(52) U.S. Cl.
CPC ............ *G06T 15/08* (2013.01); *A61B 5/0088* (2013.01); *A61B 5/4547* (2013.01); *A61B 6/032* (2013.01);
(Continued)

(58) Field of Classification Search
CPC ..... A61C 1/0007; A61C 1/0015; A61C 19/04; A61C 19/041; A61C 19/042;
(Continued)

(56) References Cited

U.S. PATENT DOCUMENTS 5,096,419 A * 3/1992 Kobayashi ............... A61C 5/02
433/72
5,295,833 A * 3/1994 Chihiro ................. A61C 19/04
433/224
(Continued)

FOREIGN PATENT DOCUMENTS

DE 10 2010 040 386 A1 3/2012
JP H09-84746 A 3/1997
(Continued)

OTHER PUBLICATIONS

Validation of Cone Beam Computed Tomography as a Tool to Explore Root Canal Anatomy—Jerome Michetti, DDS, Delphine Maret, DDS, MSc,† Jean-Philippe Mallet, DDS, MSc, and Franck Diemer, DDS, MSc, PhD‡. Journal of Endodontics—vol. 36, No. 7, Jul. 2010.*

(Continued)

*Primary Examiner* — Yogesh Patel
*Assistant Examiner* — Matthew Saunders
(74) *Attorney, Agent, or Firm* — Osha Liang LLP

(57) ABSTRACT

According to a dental image display device, a dental surgical operation device, and a dental image display method, a 2D captured image of a tooth as a surgical operation target that is captured with visible light in an articulation face direction, and an articulation face direction converted 2D image obtained as a result of displaying 3D information, which is acquired on the tooth and includes information on a root canal inside the tooth, two-dimensionally on a predetermined plane in the articulation face direction, are displayed in correspondence with each other on a monitor.

20 Claims, 24 Drawing Sheets

(51) Int. Cl.
  *A61B 6/03* (2006.01)
  *A61B 6/14* (2006.01)
  *A61B 6/00* (2006.01)
  *A61C 5/44* (2017.01)
  *A61B 5/055* (2006.01)

(52) U.S. Cl.
  CPC .............. *A61B 6/14* (2013.01); *A61B 6/463* (2013.01); *A61B 6/5247* (2013.01); *A61C 5/44* (2017.02); *A61B 5/0066* (2013.01); *A61B 5/055* (2013.01); *A61B 5/4542* (2013.01); *G06T 2200/04* (2013.01); *G06T 2215/16* (2013.01)

(58) Field of Classification Search
  CPC ........ A61B 2019/507; A61B 2019/524; A61B 2019/5291; A61B 5/4547; A61B 5/7425; A61B 5/065; A61B 6/14; A61B 6/4085; A61B 6/5247; A61B 6/4417; A61B 6/5229
  USPC .............................. 433/27; 600/427; 382/274
  See application file for complete search history.

(56) References Cited

U.S. PATENT DOCUMENTS

| | | | | |
|---|---|---|---|---|
| 5,453,009 A * | 9/1995 | Feldman | ............... | A61C 19/00 433/215 |
| 5,562,448 A * | 10/1996 | Mushabac | .......... | A61C 13/0004 433/215 |
| 5,572,566 A * | 11/1996 | Suzuki | ................... | A61B 6/145 378/98.2 |
| 6,650,928 B1 * | 11/2003 | Gailly | .................... | A61B 6/032 128/922 |
| 6,955,536 B1 * | 10/2005 | Buchanan | ........... | A61C 1/0015 433/27 |
| 7,006,862 B2 * | 2/2006 | Kaufman | ............... | A61B 6/032 378/98 |
| 8,078,000 B2 * | 12/2011 | Bohm | ...................... | G06T 5/50 382/100 |
| 8,416,984 B2 * | 4/2013 | Liang | ..................... | A61C 19/00 382/100 |
| 9,135,498 B2 * | 9/2015 | Andreiko | ........... | G06K 9/00201 |
| 9,412,166 B2 * | 8/2016 | Getto | ................ | G06T 7/0024 |
| 2002/0182564 A1 * | 12/2002 | Katsuda | ............... | A61C 1/0015 433/98 |
| 2004/0015327 A1 * | 1/2004 | Sachdeva | ................. | A61C 7/00 702/167 |
| 2005/0042572 A1 * | 2/2005 | Katsuda | ................ | A61C 1/0015 433/98 |
| 2005/0186533 A1 * | 8/2005 | Cohen | .................. | A61C 1/082 433/98 |
| 2005/0208449 A1 * | 9/2005 | Abolfathi | ................ | A61C 7/00 433/24 |
| 2007/0134613 A1 * | 6/2007 | Kuo | ........................ | A61C 7/00 433/24 |
| 2007/0238981 A1 * | 10/2007 | Zhu | ...................... | A61B 19/52 600/424 |
| 2008/0051650 A1 * | 2/2008 | Massie | .................. | A61B 6/025 600/425 |
| 2009/0177081 A1 * | 7/2009 | Joskowicz | ........... | A61B 19/201 600/426 |
| 2009/0216114 A1 * | 8/2009 | Gorges | ................... | A61B 19/52 600/425 |
| 2010/0032575 A1 * | 2/2010 | Iagaru | .................... | A61B 6/032 250/362 |
| 2011/0038514 A1 * | 2/2011 | Weigl | ................. | A61C 13/0004 382/128 |
| 2011/0256496 A1 * | 10/2011 | Arzanpour | ........... | A61C 1/0007 433/27 |
| 2012/0015316 A1 * | 1/2012 | Sachdeva | ............. | A61C 19/045 433/24 |
| 2012/0015329 A1 * | 1/2012 | Gross | ..................... | A61C 1/084 433/215 |
| 2012/0065943 A1 * | 3/2012 | Fisker | ................ | A61C 13/0004 703/1 |
| 2012/0100500 A1 * | 4/2012 | Gao | ........................ | A61C 1/084 433/72 |
| 2012/0214121 A1 * | 8/2012 | Greenberg | ........... | A61B 5/0088 433/24 |
| 2012/0230567 A1 * | 9/2012 | Greenberg | ............... | A61B 6/14 382/131 |
| 2013/0108011 A1 * | 5/2013 | Sadakane | ................. | A61B 6/03 378/19 |
| 2013/0163718 A1 | 6/2013 | Lindenberg et al. | | |
| 2013/0171580 A1 * | 7/2013 | Van Lierde | .............. | A61B 6/14 433/29 |
| 2013/0243276 A1 * | 9/2013 | Souza | ................... | G06T 7/0081 382/128 |
| 2013/0294666 A1 * | 11/2013 | Bultema | .................. | A61B 6/14 382/131 |
| 2013/0308846 A1 * | 11/2013 | Chen | .................... | G06T 7/0012 382/131 |
| 2014/0141385 A1 * | 5/2014 | Taub | ....................... | A61C 3/02 433/27 |
| 2014/0186794 A1 * | 7/2014 | Deichmann | .......... | A61B 17/176 433/75 |
| 2014/0228992 A1 * | 8/2014 | Van Lierde | .......... | G09B 23/283 700/98 |
| 2014/0272772 A1 * | 9/2014 | Andreiko | ............... | A61C 7/002 433/29 |
| 2014/0314291 A1 * | 10/2014 | Souza | ................... | G06T 7/0012 382/131 |

FOREIGN PATENT DOCUMENTS

| | | | |
|---|---|---|---|
| JP | 2003-019143 A | | 1/2003 |
| JP | 2006-305203 A | | 11/2006 |
| JP | 2009-153785 A | | 7/2009 |
| JP | 2010-246855 A | | 11/2010 |
| JP | 2011-030637 A | | 2/2011 |
| JP | 2011-212367 A | | 10/2011 |
| JP | 2011212367 | * | 10/2011 |
| JP | 5016311 B2 | | 9/2012 |
| WO | 2012/155998 A1 | | 11/2012 |
| WO | WO 2012155998 A1 * | 11/2012 | ......... G06F 19/3437 |

OTHER PUBLICATIONS

Identification of dental root canals and their medial line from micro-CT and cone-beam CT records-Balázs Benyó. BioMedical Engineering OnLine 2012, 11:81.*

* cited by examiner

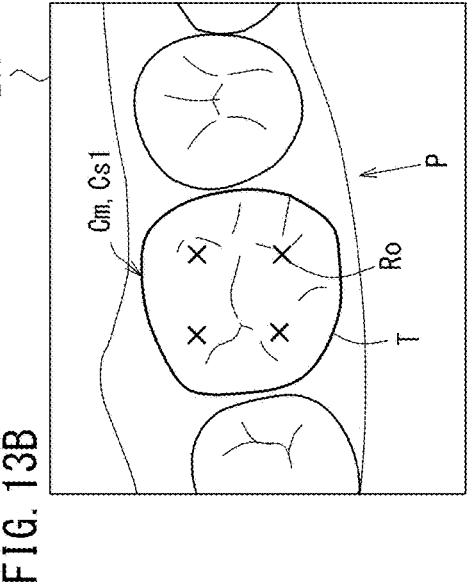
FIG. 13A
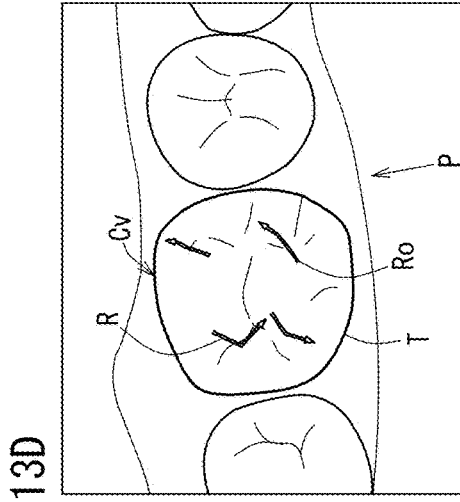
FIG. 13B
FIG. 13C
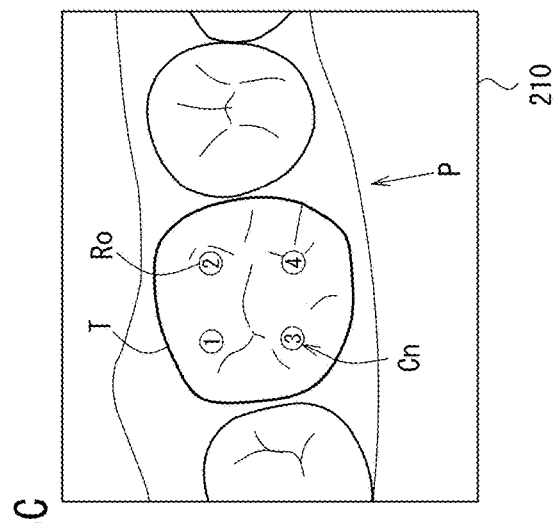
FIG. 13D

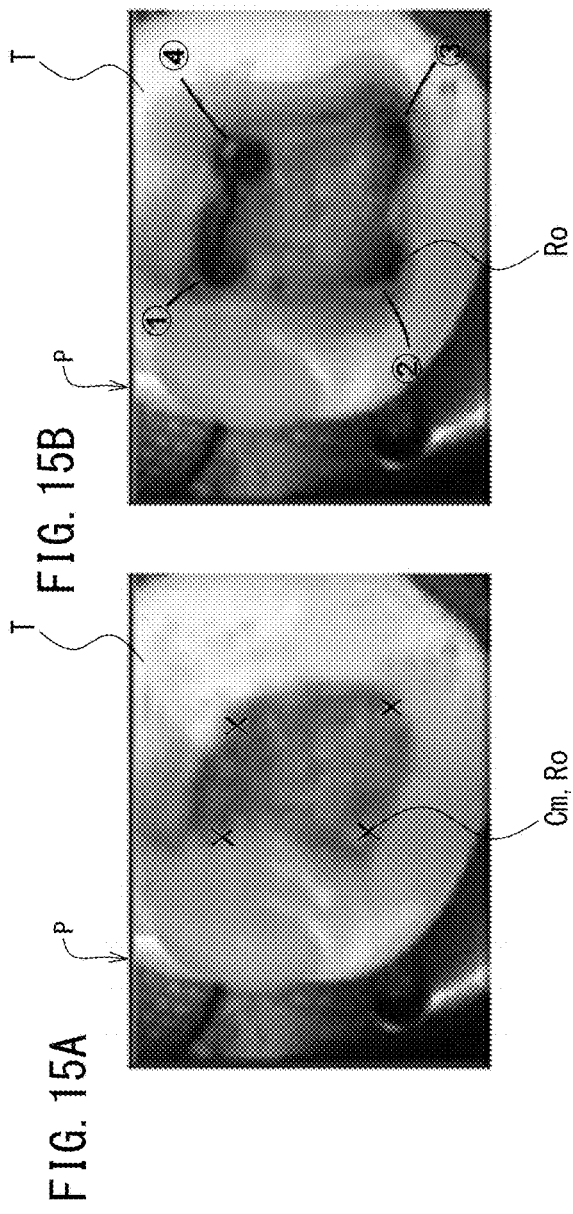

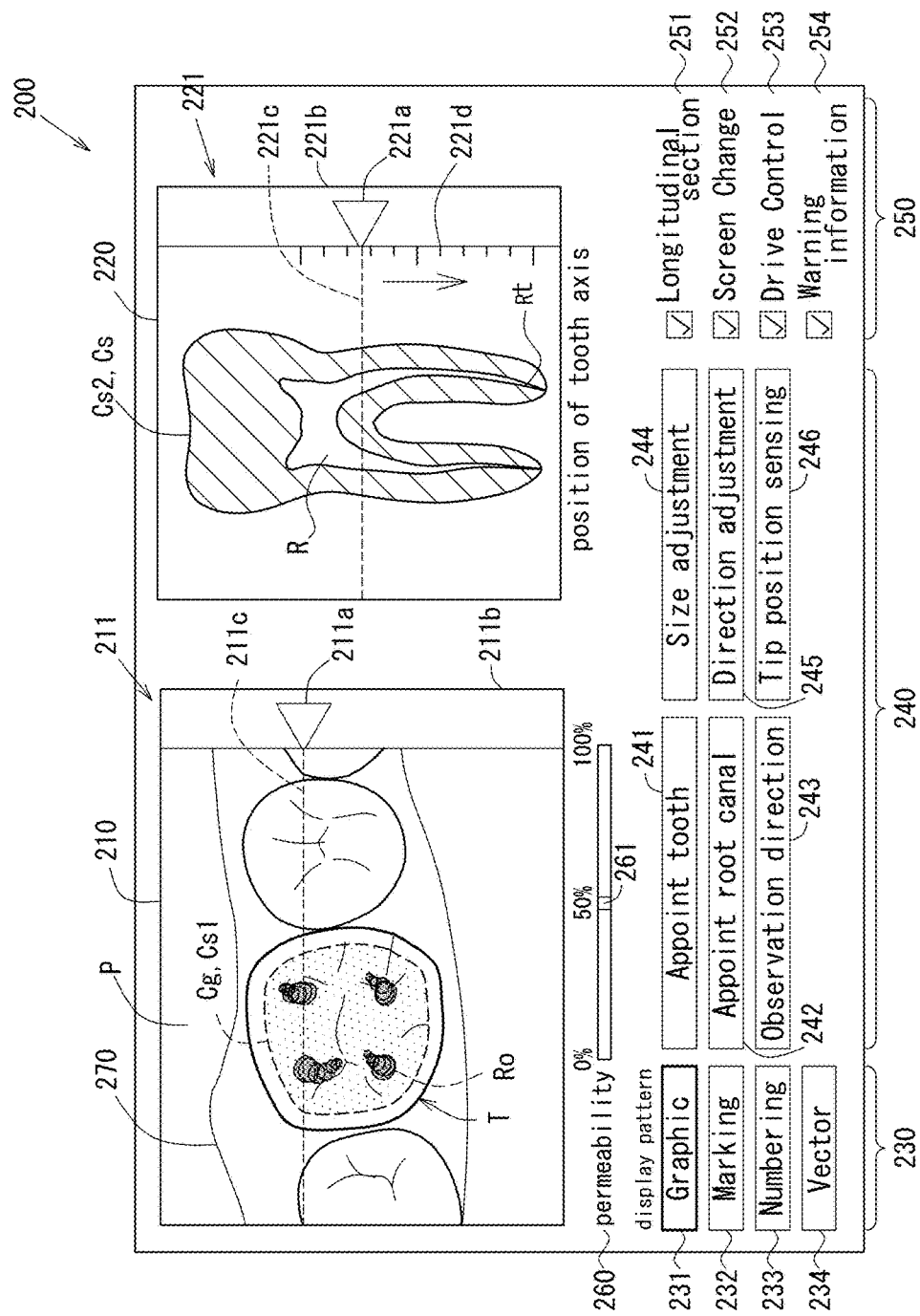

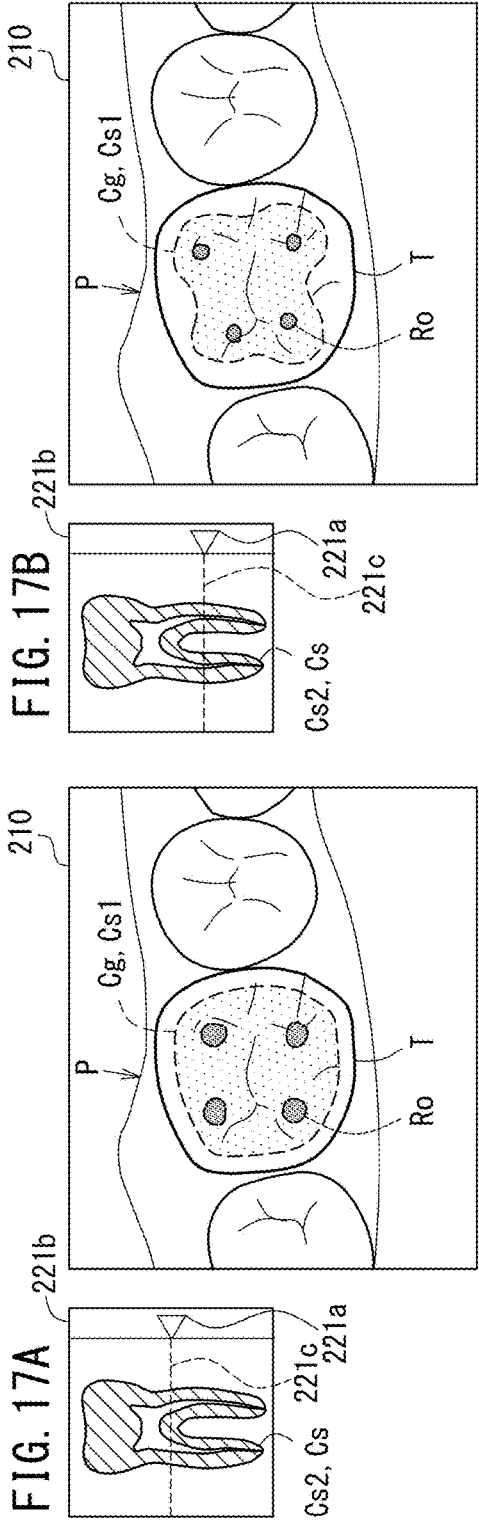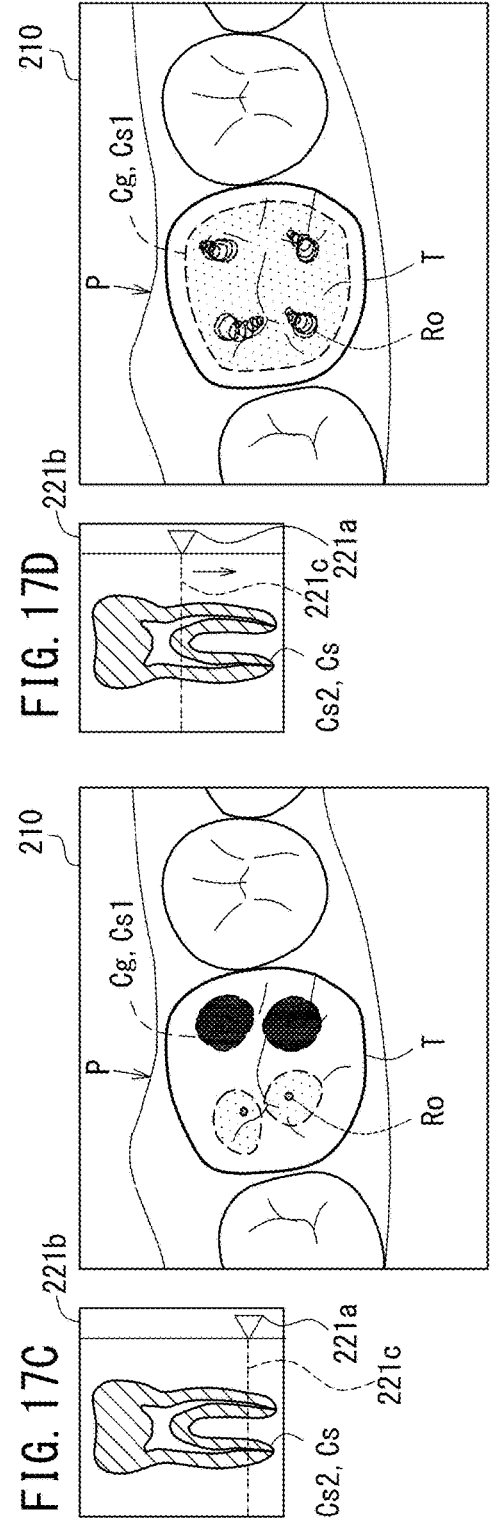

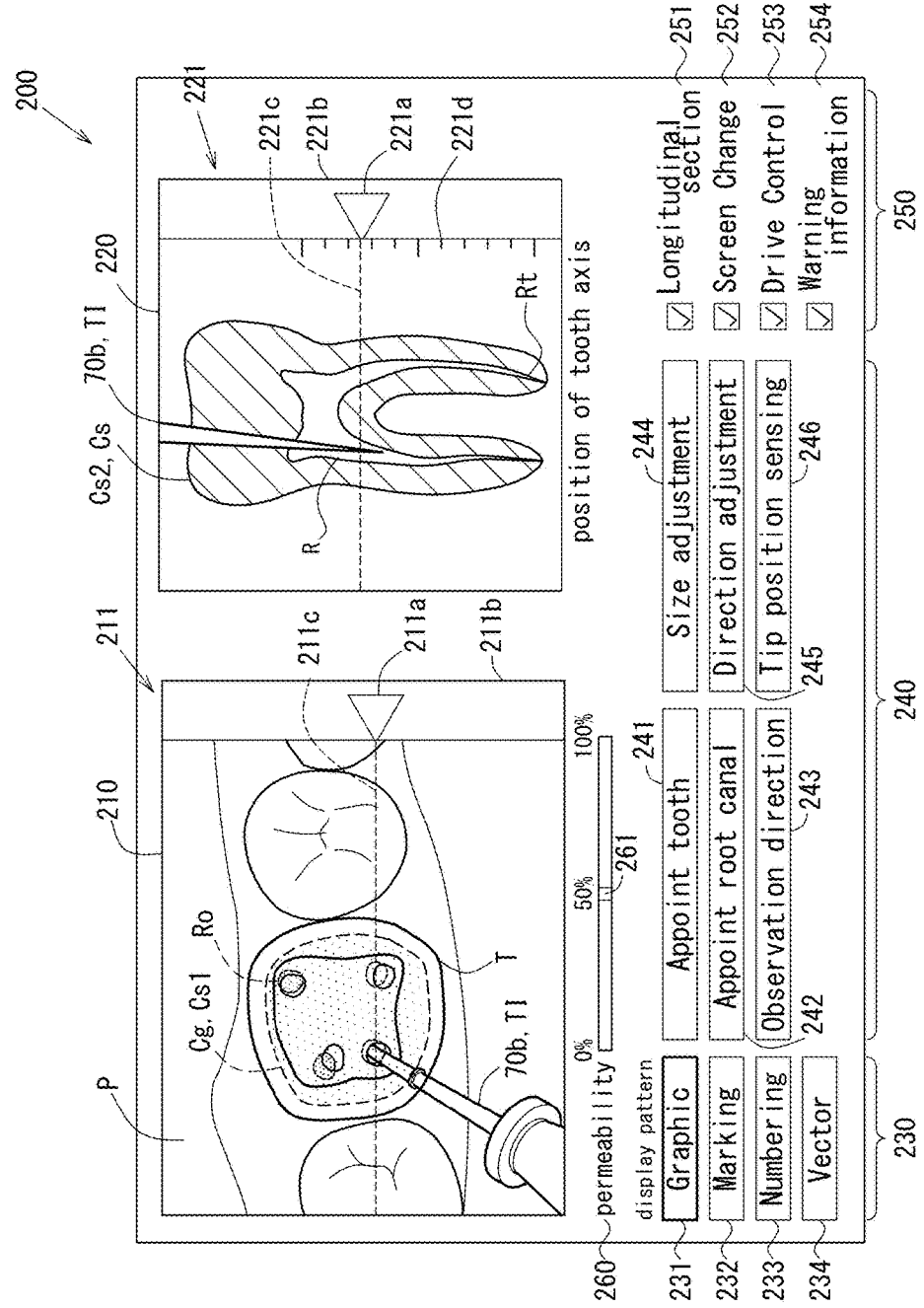

DENTAL IMAGE DISPLAY DEVICE, DENTAL SURGICAL OPERATION DEVICE, AND DENTAL IMAGE DISPLAY METHOD

CROSS-REFERENCE TO RELATED APPLICATIONS

The present application claims benefit of priority under 35 U.S.C. § 119 to Japanese Patent Application No. 2013-043707 filed on Mar. 6, 2013. The contents of the priority applications are incorporated by reference in their entirety.

BACKGROUND OF THE INVENTION

1. Field of the Invention

The present invention relates to a dental image display device, a dental surgical operation device, and a dental image display method for displaying a two-dimensional image of a tooth captured with visible light in an articulation face direction by an optical camera and also displaying two-dimensional display information generated based on three-dimensional information which is captured by an X-ray CT image capturing device or MRI and includes information on a root canal inside the tooth.

2. Description of the Prior Art

Conventionally, in the fields of dental care and the like, an image of a tooth is captured as follows for performing a surgical operation on a tooth for the purpose of root canal treatment or the like. An image of a tooth is captured by an optical camera generally referred to as an "intraoral camera" in a direction in which the articulation face is observed (hereinafter, referred to as a "direction of an articulation face" or an "articulation face direction"), or a tooth is observed by a microscope or the like in the articulation face direction. In this manner, the root canal treatment is performed precisely.

However, an image captured by an optical camera or an image observed by a microscope or the like in the articulation face direction is an image of a surface of the tooth captured with visible light in the articulation face direction. In the image captured with visible light, the root canal or the like inside the tooth cannot be observed.

In an improved system, CT (computerized tomography) image capturing is performed. According to the CT image capturing, an X ray is directed toward a tooth which is a target of interest to collect projection data, and the obtained projection data is re-constructed on a computer to generate a CT image (volume rendering image, etc.).

The CT image capturing is performed as follows. A subject is located between an X-ray generator and an X-ray detector. While the X-ray generator and the X-ray detector are revolved around the subject, a cone-like X-ray is directed toward the subject from the X-ray generator. The X-ray detection results are collected by X-ray detector, and three-dimensional data is re-constructed based on the collected X-ray detection results. A device usable for performing such CT image capturing is disclosed in, for example, Patent Document 1.

An X-ray CT image capturing device disclosed in Patent Document 1 displays a volume rendering image in addition to a cross-sectional view taken along each of X, Y and Z directions. An X cursor, a Y cursor and a Z cursor are operated to display cross-sections corresponding to the respective cursors.

In such CT image capturing, information on the tooth acquired by the X-ray transmitted through the tooth includes information on the root canal inside the tooth. Therefore, the position or size of the root canal orifice or the like, which cannot be visually recognized from the surface, can be shown.

However, as described above, the operator needs to perform a treatment while checking the image captured by the optical camera or the microscope. Therefore, the operator needs to imagine synthesizing the CT image and the image captured by the optical camera or the microscope three-dimensionally while performing the treatment. For example, it is difficult to accurately grasp the position of the root canal orifice inside the tooth while checking an image of the surface of the tooth captured by the optical camera or the microscope. There is a risk that the root canal is excessively cut even into the healthy area other than the root canal orifice, which may result in the breakage of the tooth referred to as "root canal fracture".

PRIOR ART DOCUMENT

Patent Document

Patent Document 1: Japanese Laid-Open Patent Publication No. 2006-305203

SUMMARY OF THE INVENTION

One or more embodiments of the present invention provide a dental image display device, a dental surgical operation device, and a dental image display method for clearly showing a root canal inside a tooth on a two-dimensional image captured with visible light.

One or more embodiments of the present invention are directed to a dental image display device and a dental image display method for displaying a two-dimensional captured image captured by visible light and two-dimensional display information in correspondence with each other on a display section. The two-dimensional captured image captured by visible light is obtained as a result of capturing a tooth which is a target of interest in a direction of an articulation face, and the two-dimensional display information is obtained as a result of displaying three-dimensional information on the tooth two-dimensionally along a predetermined plane, the three-dimensional information containing information on a root canal inside the tooth.

The "direction of the articulation face" or "articulation face direction" is a planar direction in which the articulation face expands, and refers to a two-dimensional direction of the articulation face to be observed. Based on the tooth axis, the "direction of the articulation face" is a direction of the face which is observed in the tooth axis direction. More specifically, the "direction of the articulation face" encompasses a range of directions of the face which is observed in a direction crossing the tooth axis at an angle of ±30 degrees. "Capturing an image in the articulation face direction" refers to capturing an image in a line-of-sight direction in which the articulation face is observed. This direction is, preferably, a line-of-sight direction confronting the articulation face and/or the line-of-sight direction in which a plan view of the teeth on the lower jaw is seen and a bottom view of the teeth in the upper jaw is seen. The line-of-sight direction may be perpendicular to the direction of the articulation face direction and may be inclined with respect to the perpendicular direction at ±30 degrees.

The "predetermined plane" refers to a plane in the direction the articulation face or a plane crossing such a plane. The "predetermined plane" encompasses a cross-section passing the inside of a tooth and also a plane which is not visually recognizable, namely, a non-exposed surface of the tooth or a plane separated from the surface of the tooth.

The three-dimensional information acquired on the tooth that includes information on the root canal inside the tooth may be information acquired by an X-ray CT image capturing device, an MRI image capturing device or an optical coherence tomography (OCT) image capturing device. The X-ray CT image capturing device may perform CT image capturing over a range of angles of about 180 degrees or about 360 degrees.

Owing to the above, the root canal inside the tooth is clearly shown on the two-dimensional captured image captured with visible light.

This will be described in more detail. The two-dimensional captured image and the two-dimensional display information are displayed in correspondence with each other on the display section. The two-dimensional captured is of a tooth as a target of interest that is captured with visible light in the articulation face direction. The two-dimensional display information is obtained as a result of displaying three-dimensional information, which is acquired on the tooth and includes information on the root canal inside the tooth, two-dimensionally on a predetermined plane. Therefore, the two-dimensional display information obtained as a result of displaying the three-dimensional information two-dimensionally on the predetermined plane can show, for example, the position or size of the root canal inside the tooth, and thus clearly show the root canal or the like inside the tooth, on the two-dimensional captured image of a surface of the tooth that is captured with visible light. Therefore, an operator can perform an accurate surgical operation while checking the two-dimensional captured image showing the surface of the tooth and also grasping the position, size or direction of the root canal inside the tooth.

In one or more embodiments of the present invention, the predetermined plane may be a plane parallel to the direction of the articulation face; and the dental image display device may include an adjustment section that adjusts at least one of the two-dimensional display information and the two-dimensional captured image such that the two-dimensional display information and the two-dimensional captured image are aligned with each other.

The "plane parallel to the direction of the articulation face" is not limited to a direction strictly parallel to the articulation face direction. The "plane parallel to the articulation face direction" encompasses a range of directions in which a line vertical to the articulation face direction and a line vertical to the predetermined plane cross each other at ±30 degrees under the condition that the articulation face and the plane are oriented in the same direction. In other words, the "plane parallel to the articulation face direction" is a plane crossing the articulation face direction at ±30 degrees or less.

The "adjustment section that adjusts at least one of the two-dimensional display information and the two-dimensional captured image such that the two-dimensional display information and the two-dimensional captured image are accommodated to each other" is an adjustment section that adjusts the size, direction or position of the two-dimensional display information or the two-dimensional captured image such that the two-dimensional display information and the two-dimensional captured image are comparable with each other. The above-described adjustment section encompasses an adjustment section that adjusts the size, direction or position of the two-dimensional display information with respect to the two-dimensional captured image, an adjustment section that adjusts the size, direction or position of the two-dimensional captured image with respect to the two-dimensional display information, or an adjustment section that adjusts the size, direction or position of both of the two-dimensional display information and the two-dimensional captured image with respect to each other.

Owing to the above, the two-dimensional display information is adjusted by the adjustment section to be comparable with the two-dimensional captured image. Thus, an accurate position of the root canal can be grasped.

In one or more embodiments of the present invention, the information on the root canal may contain information on a root canal site and/or a root canal orifice; and the root canal site and/or the root canal orifice may be colored or marked.

The coloring and/or marking encompasses, for example, coloring the root canal site and/or the root canal orifice, displaying the profile of the root canal site and/or the root canal orifice, numbering the root canal site and/or the root canal orifice, displaying the position of the root canal site and/or the root canal orifice by "x", displaying the direction of the root apex with respect to the root canal orifice by an arrow, and other appropriate display methods.

Owing to the above, the position, size or direction of the root canal orifice or the root canal site can be perceived intuitively.

In one or more embodiments of the present invention, the two-dimensional display information and the two-dimensional captured image aligned with each other by the adjustment section may be displayed in an overlapping manner and visually recognizably.

"Displaying the two-dimensional display information and the two-dimensional captured image in an overlapping manner and visually recognizably" refers to displaying the two-dimensional display information and the two-dimensional captured image, which are adjusted in terms of the size and direction, in an overlapping manner, and encompasses displaying the two-dimensional display information and the two-dimensional captured image such that both of the information and the image are visually recognizable by an appropriate display method. Such display may be performed in the following manners, for example. Only the marking or coloring showing the root canal based on the two-dimensional display information is displayed as overlapping the two-dimensional captured image. Among the two-dimensional display information and the two-dimensional captured image displayed in an overlapping manner, one of the image and the information which overlaps the other is displayed in a semi-permeable state so that the other of the image and the information is visually recognizable. Among the two-dimensional display information and the two-dimensional captured image displayed in an overlapping manner, one of the image and the information which is represented by a profile is displayed as overlapping the other so that the other of the image and the information is visually recognizable.

Owing to the above, the two-dimensional display information and the two-dimensional captured image are displayed in an overlapping state. Thus, the position, size or direction of the root canal with respect to the tooth in the two-dimensional captured image can be shown more accurately.

In one or more embodiments of the present invention, the two-dimensional display information and the two-dimensional captured image aligned with each other by the adjustment section may be displayed on one, same display section in a switched manner or concurrently side by side.

Owing to this, the two-dimensional display information and the two-dimensional captured image are displayed in a switched manner or concurrently side by side. Thus, the two-dimensional display information and the two-dimensional captured image can each be displayed clearly, and the position, size or direction of the root canal with respect to the tooth in the two-dimensional captured image can be shown more accurately.

In one or more embodiments of the present invention, the two-dimensional display information may be two-dimensional image display information obtained as a result of forming the two-dimensional display information into an image.

Owing to this, the two-dimensional captured image and the two-dimensional display information are easily compared with each other. Thus, the position, size or direction of the root canal with respect to the tooth in the two-dimensional captured image can be shown more accurately.

In one or more embodiments of the present invention, the dental image display device may further include a tooth axis direction display position adjustment section that adjusts a position of the predetermined plane in a tooth axis direction which is perpendicular to the direction of the articulation face.

Owing to this, the two-dimensional display information at a predetermined position in the tooth axis direction is displayed. Thus, for example, during the root canal treatment, the position of the root canal in the articulation face direction can be continuously displayed while being changed along the tooth axis direction, so that the operator can check the direction of the root canal.

In one or more embodiments of the present invention, the dental image display device may include a three-dimensional information storage section that stores the three-dimensional information; and a two-dimensional display information generation section that generates the two-dimensional display information based on the three-dimensional information stored on the three-dimensional information storage section.

Owing to this, for example, the three-dimensional information acquired by the X-ray CT image capturing device or the like is stored on the three-dimensional information storage section, and the three-dimensional information stored on the three-dimensional information storage section is read so that the two-dimensional display information is generated by the two-dimensional display information generation section and displayed.

In one or more embodiments of the present invention, the dental image display device may further include a tooth specification section that specifies a tooth which is a target of interest from the two-dimensional captured image; and a corresponding information extraction section that extracts three-dimensional information corresponding to the tooth specified by the tooth specification section among the three-dimensional information stored on the three-dimensional information storage section.

Owing to this, for example, the tooth which is a surgical operation target or a target of interest is specified by the tooth specification section from the two-dimensional captured image showing a plurality of teeth and the gum, and the three-dimensional information on the specified tooth is extracted. The two-dimensional display information based on the three-dimensional information on the tooth is displayed. Therefore, even when the two-dimensional captured image shows elements other than the target of interest, the two-dimensional display information of the tooth as the target of interest can be displayed with certainty.

In one or more embodiments of the present invention, the dental image display device may include a two-dimensional captured image storage section that stores the two-dimensional captured image.

Owing to this, the two-dimensional captured image stored on the two-dimensional information storage section is read and displayed as the two-dimensional display information. Therefore, the two-dimensional captured image captured by an optical camera such as an intraoral camera or the like or by a microscope can be displayed on another display device such as a monitor or the like.

In one or more embodiments of the present invention, the predetermined plane may be a cross-section in a tooth axis direction along a tooth axis of the tooth; and the two-dimensional display information may be two-dimensional cross-section display information along the cross-section in the tooth axis direction, and is displayed concurrently with the two-dimensional captured image.

Owing to this, for example, during the root canal treatment, the position of the tip of site treated by the surgical operation tool can be checked with the two-dimensional cross-section display information in the tooth axis direction.

In one or more embodiments of the present invention, the two-dimensional cross-section display information and the two-dimensional display information along a plane parallel to the articulation face may be displayed concurrently.

Owing to this, the two-dimensional display information in a direction parallel to the articulation face direction, which is generated based on the three-dimensional, the two-dimensional cross-section display information in the tooth axis direction, and the two-dimensional captured image can be displayed concurrently and compared with one another.

In one or more embodiments of the present invention, the two-dimensional cross-section display information in the tooth axis direction may be displayed together with a scale that displays a distance from a root apex to a tooth crown.

Owing to this, for example, the distance from the tip of the surgical operation tool to the root apex can be checked.

One or more embodiments of the present invention are directed to a dental surgical operation device including a dental image display device described above; and a surgical operation tool usable to perform a surgical operation on the tooth.

The surgical operation tool may be a reamer, a file or a cutting tool.

Owing to this, the operator can perform an accurate surgical operation by use of the surgical operation tool while checking the two-dimensional display information and the two-dimensional captured image displayed on the dental image display device.

In one or more embodiments of the present invention, the dental surgical operation device may further include a detection section that detects a position of a tip of the surgical operation tool in the tooth. The predetermined plane may be a plane at a position corresponding to the position of the tip detected by the detection section.

Owing to this, the two-dimensional display information at the position of the tip of the surgical operation tool is displayed. Therefore, the surgical operation can be performed more accurately and safely.

In one or more embodiments of the present invention, the dental surgical operation device may further include a root canal length measurement device that detects a root canal length; a root canal length information storage section that stores root canal length information detected by the root canal length measurement device; and an operation section that performs a predetermined operation when the position of the tip detected by the detection section is a predetermined position with respect to the root canal length information stored on the root canal length information storage section.

The root canal length measurement device that detects a root canal length may measure the distance from the root canal orifice to the root apex, and also the distance from the root canal orifice to a position away from the root apex toward the operator by a predetermined distance. The operation section, that performs a predetermined operation when the position of the tip of the surgical operation tool reaches a predetermined position with respect to the root canal length information, can perform the operation when the tip is at a position away from the root apex toward the operator; namely, can perform the operation without the tip reaching the root apex. The position of the tip away from the root apex toward the operator may be set by the operator. The root canal length measurement device may be one device included in the dental surgical operation device, and may be built in, for example, the cutting tool.

Owing to this, the predetermined operation may be performed based on the tip approaching the root apex.

In one or more embodiments of the present invention, the operation section may include a notification section that notifies that the position of the tip may be at the predetermined position with respect to the root canal length information.

Owing to this, for example, it is notified by voice, buzzer, melody, vibration, lighting of an LED or the like, blinking of light or the like that the tip is at a position away from the root apex toward the operator by a few millimeters. Therefore, the operator can recognize that the tip has approached the root apex and thus can perform the surgical operation carefully and cautiously.

In one or more embodiments of the present invention, the operation section may include a driving control section that controls driving of the surgical operation device.

"Controlling the driving of the surgical operation device" encompasses stopping the driving of the surgical operation device, decreasing the output thereof, oppositely rotating the surgical operation device in the case where the surgical operation device is driven to rotate, and other manners of driving control.

Owing to this, for example, the driving of the surgical operation device is controlled at a position away from the root apex toward the operator by a few millimeters. Therefore, the driving can be controlled to avoid so-called perforation, which means that the cutting tool pierces the root apex. Thus, the surgical operation can be performed safely.

In one or more embodiments of the present invention, the dental surgical operation device may further include a root canal route information storage section that stores root canal route information on a route of the root canal based on the three-dimensional information; and a route deviation detection section that detects that a tip of the surgical operation tool has deviated from a predetermined route of the root canal.

Owing to this, for example, even when the route of the sub root canal or the like is complicated, the surgical operation can be performed safely.

In one or more embodiments of the present invention, the dental surgical operation device may further include a driving control section that controls the driving of the surgical operation tool based on the detection of the deviation of the tip of the surgical operation tool by the route deviation detection section.

Owing to this, when the surgical operation tool is deviated from the route, the driving of the surgical operation tool is controlled. Therefore, even when the route of the root canal is complicated, the surgical operation can be performed accurately along a predetermined route.

In one or more embodiments of the present invention, the dental surgical operation device may further include a deviation notification section that performs a notification based on the detection of the deviation of the tip of the surgical operation tool by the route deviation detection section.

Owing to this, when the surgical operation tool is deviated from the route, the deviation is notified by voice, buzzer, melody, vibration, lighting of an LED or the like, blinking of light or the like. Therefore, even when the route of the root canal is complicated, the surgical operation tool is not deviated from the route, and the surgical operation can be performed accurately.

In one or more embodiments of the present invention, the dental surgical operation device may further include an output detection section that detects a rotation torque or a vibration output of the surgical operation tool; and a driving control section that controls the driving of the surgical operation tool when the rotation torque or the vibration output detected by the output detection section reaches a value stored in advance.

Owing to this, a state where the surgical operation tool is broken due to excessive load and remains in the root canal is prevented. Thus, the surgical operation can be performed safely.

One or more embodiments of the claimed invention provide a dental image display device, a dental surgical operation device, and a dental image display method for clearly showing a root canal inside a tooth on a two-dimensional image captured with visible light.

BRIEF DESCRIPTION OF DRAWINGS

FIGS. 13A, 13B, 13C, and 13D show overlapping display patterns.

FIGS. 15A and 15B provide photographs with overlapping display.

FIG. 16 shows a display position adjustment scroll bar on the image overlapping display screen.

FIGS. 17A, 17B, 17C, and 17D show display position adjustment in a tooth axis direction.

FIG. 19 shows display of a tip of a surgical operation tool on the image overlapping display screen.

DESCRIPTION OF THE PREFERRED EMBODIMENTS

Hereinafter, a medical care system 1 according to one or more embodiments of the present invention will be described with reference to FIG. 1 through FIG. 19.

Figure 1:
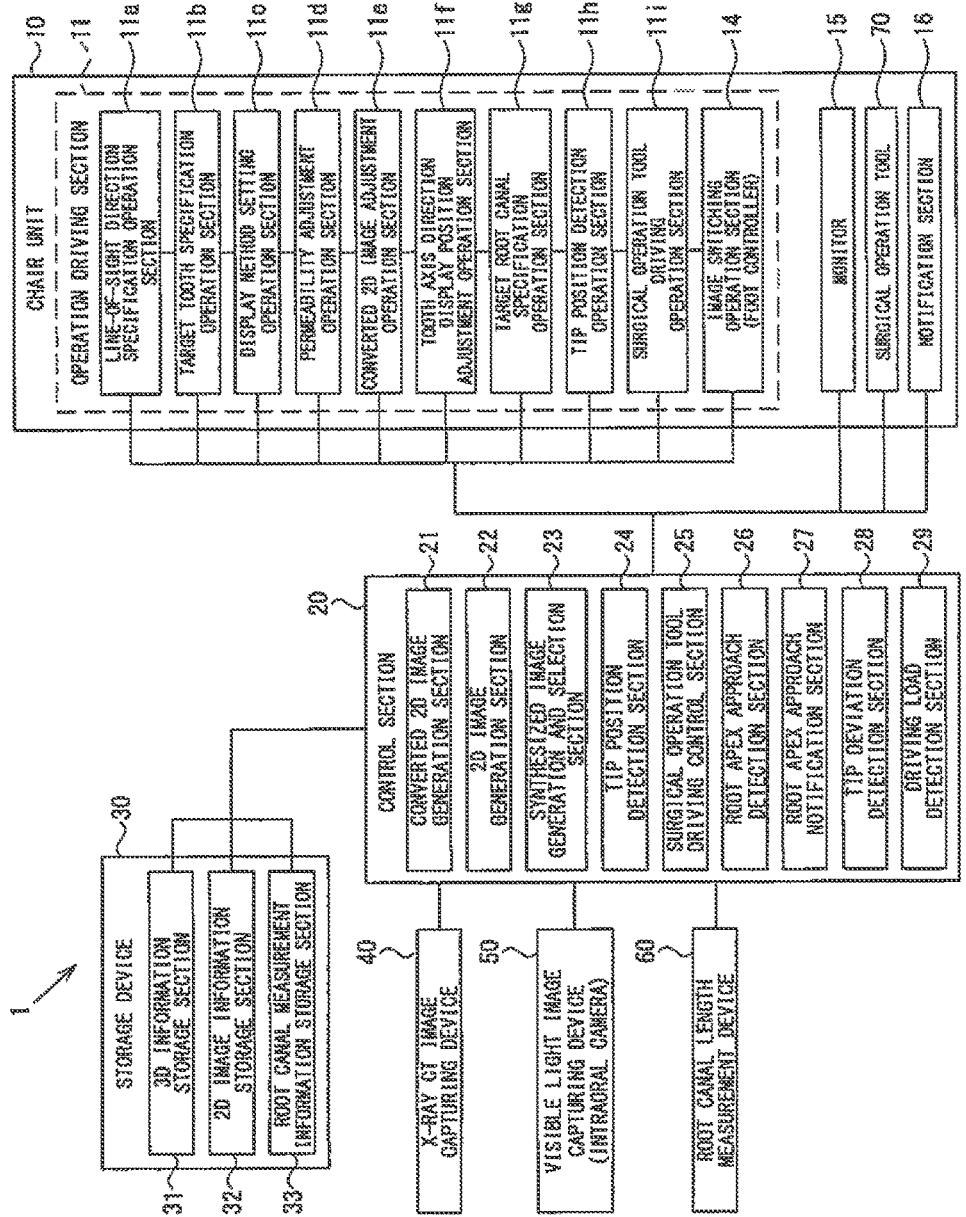
FIG. 1 is a block diagram of a medical care system.
Figure 2:
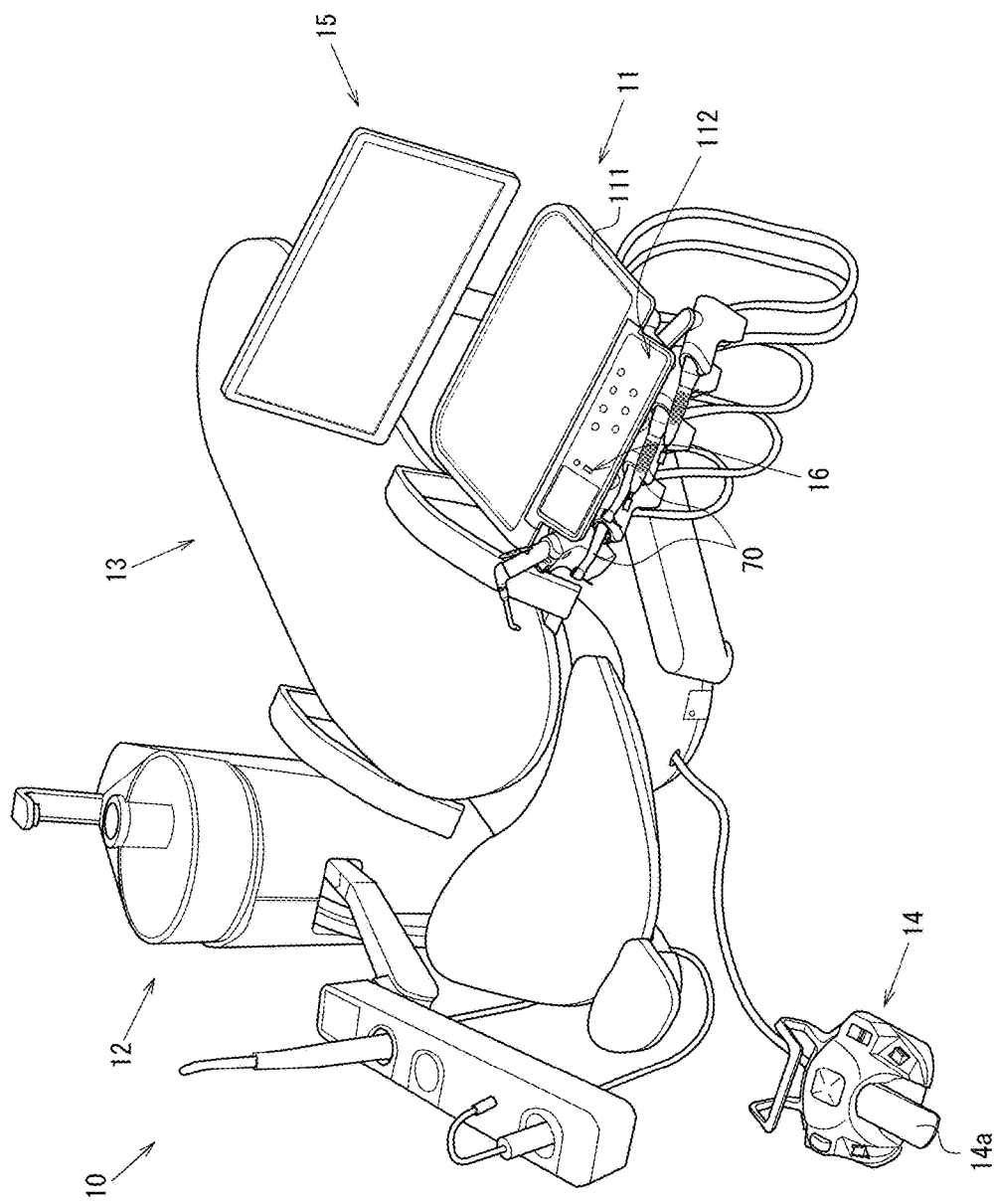
FIG. 2 is a schematic isometric view showing a structure of a chair unit.
Figure 3:
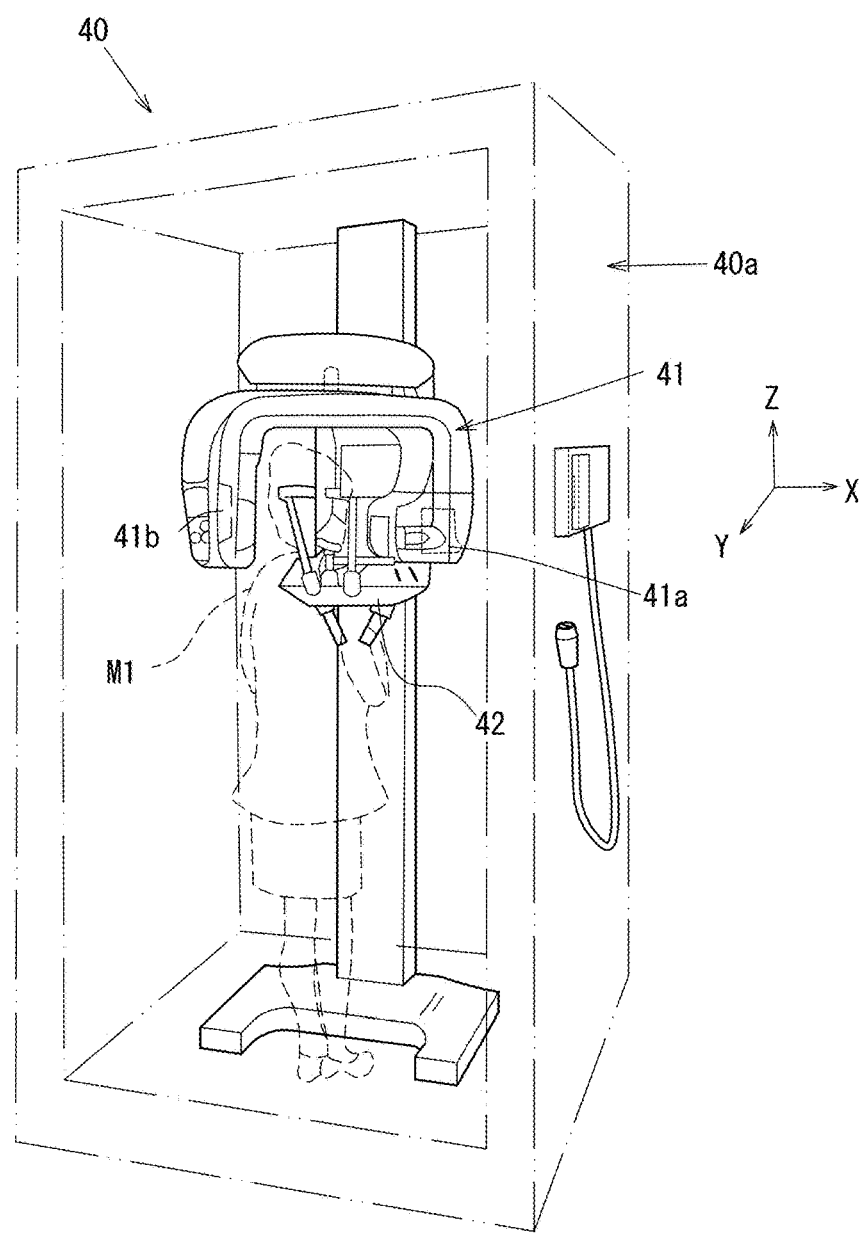
FIG. 3 a schematic isometric view of an X-ray image capturing device.
Figure 4:
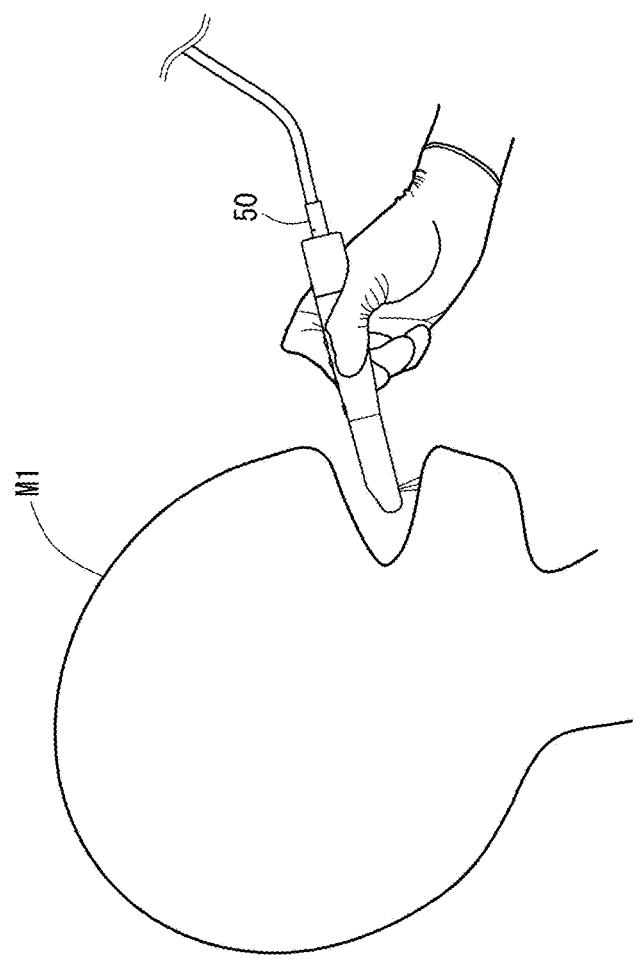
FIG. 4 is a schematic view of an intraoral camera.
Figure 5:
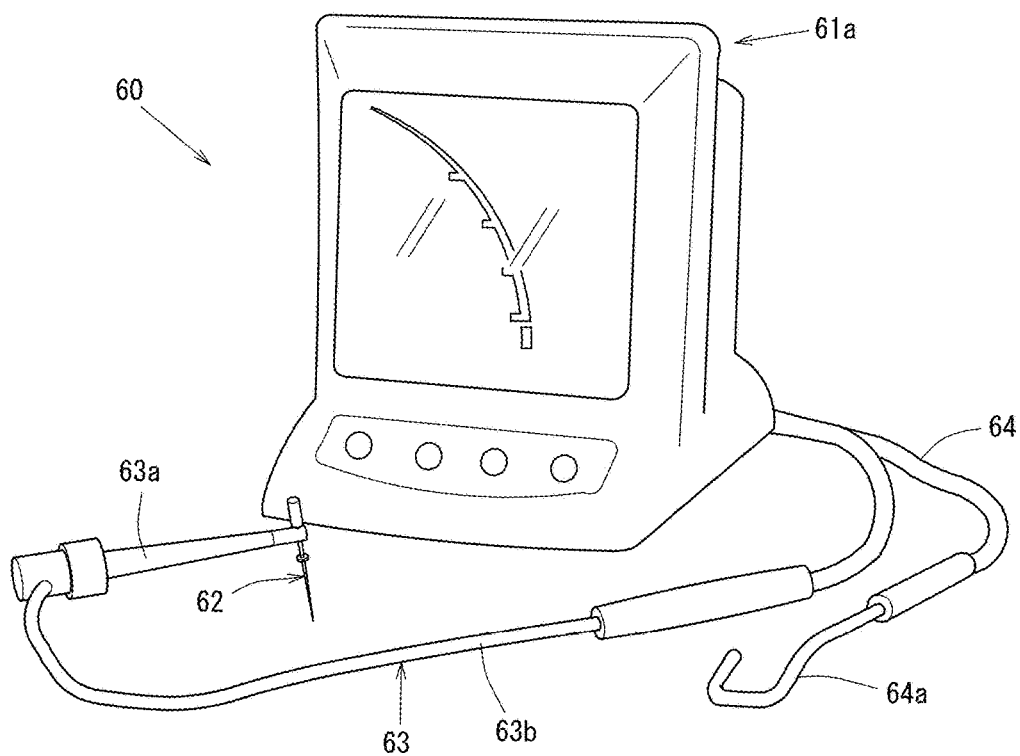
FIG. 5 is a schematic isometric view of a root canal length measurement device.
Figure 6:
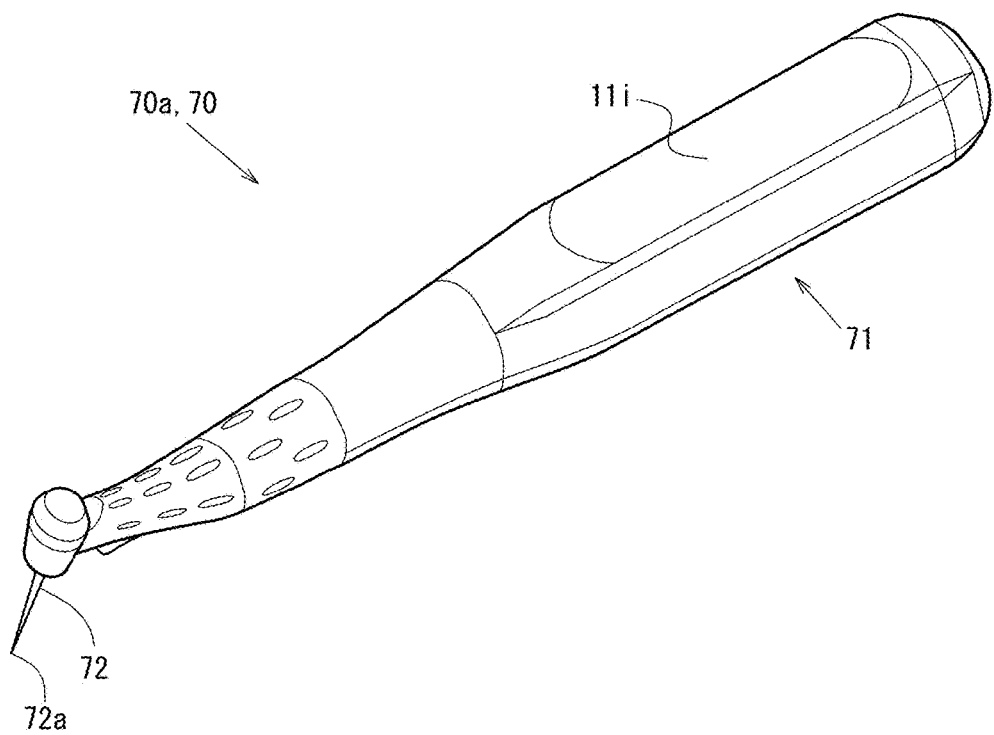
FIG. 6 is a schematic isometric view of a root canal treating hand piece.
Figure 7:
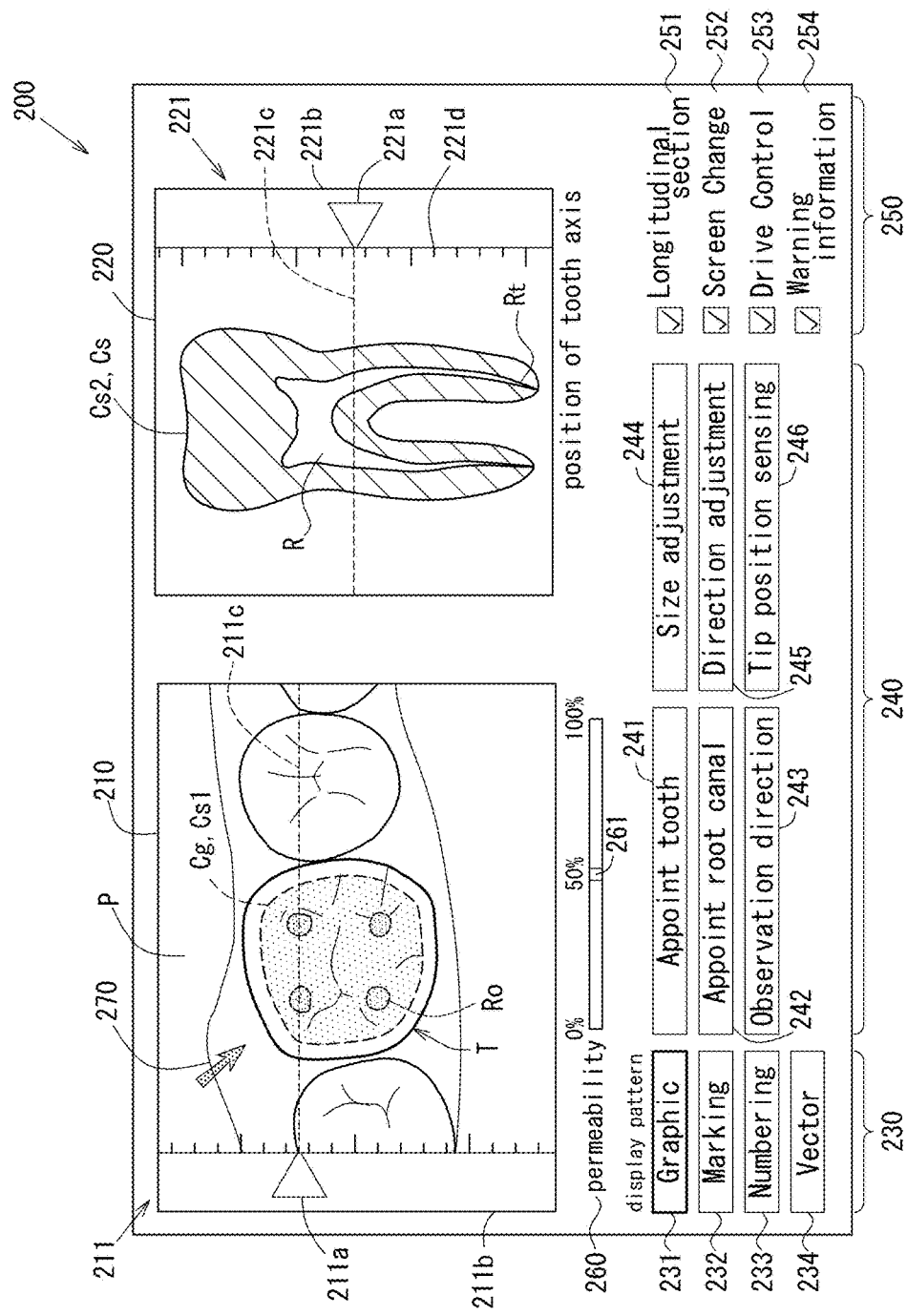
FIG. 7 shows an image overlapping display screen.

FIG. 1 is a block diagram of the medical care system 1, and FIG. 2 is a schematic isometric view showing a structure of a chair unit 10. FIG. 3 is a schematic isometric view of an X-ray CT image capturing device 40. FIG. 4 is a schematic view of an intraoral camera 50. FIG. 5 is a schematic isometric view of a root canal length measurement device 60. FIG. 6 is schematic isometric view of a surgical operation tool 70. FIG. 7 shows an image overlapping display screen 200.

Figure 8:
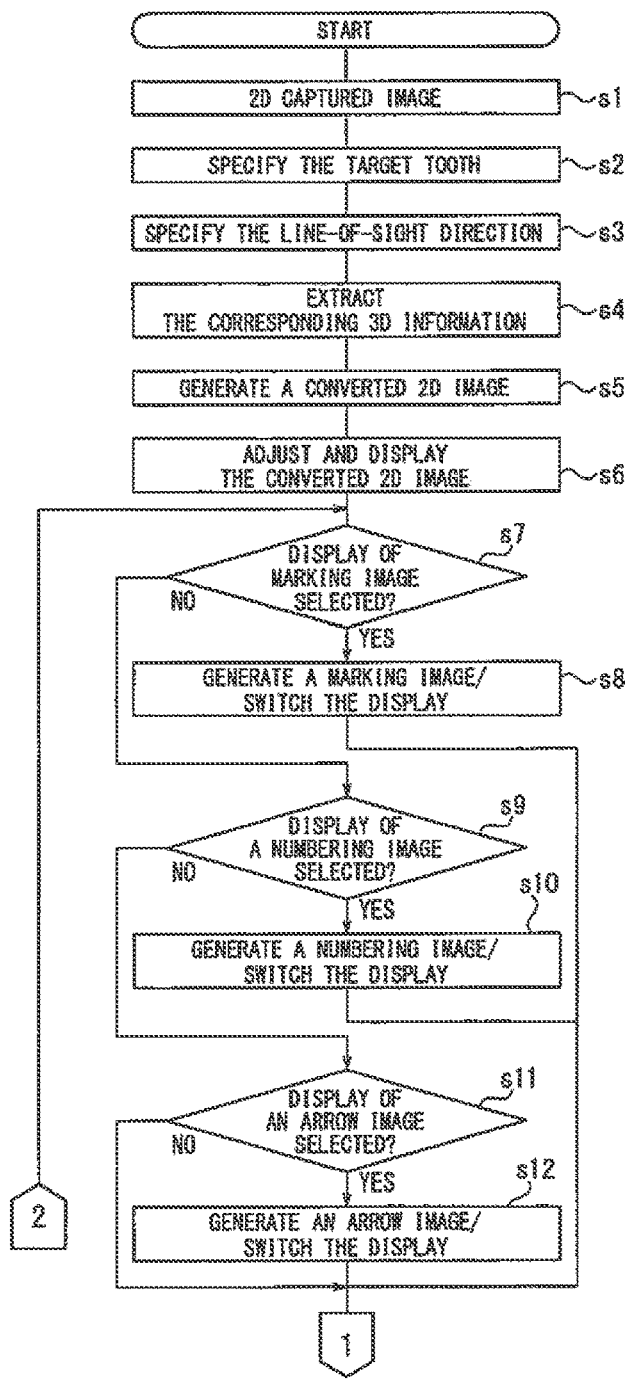
FIG. 8 is a flowchart showing a dental care process.
Figure 9:
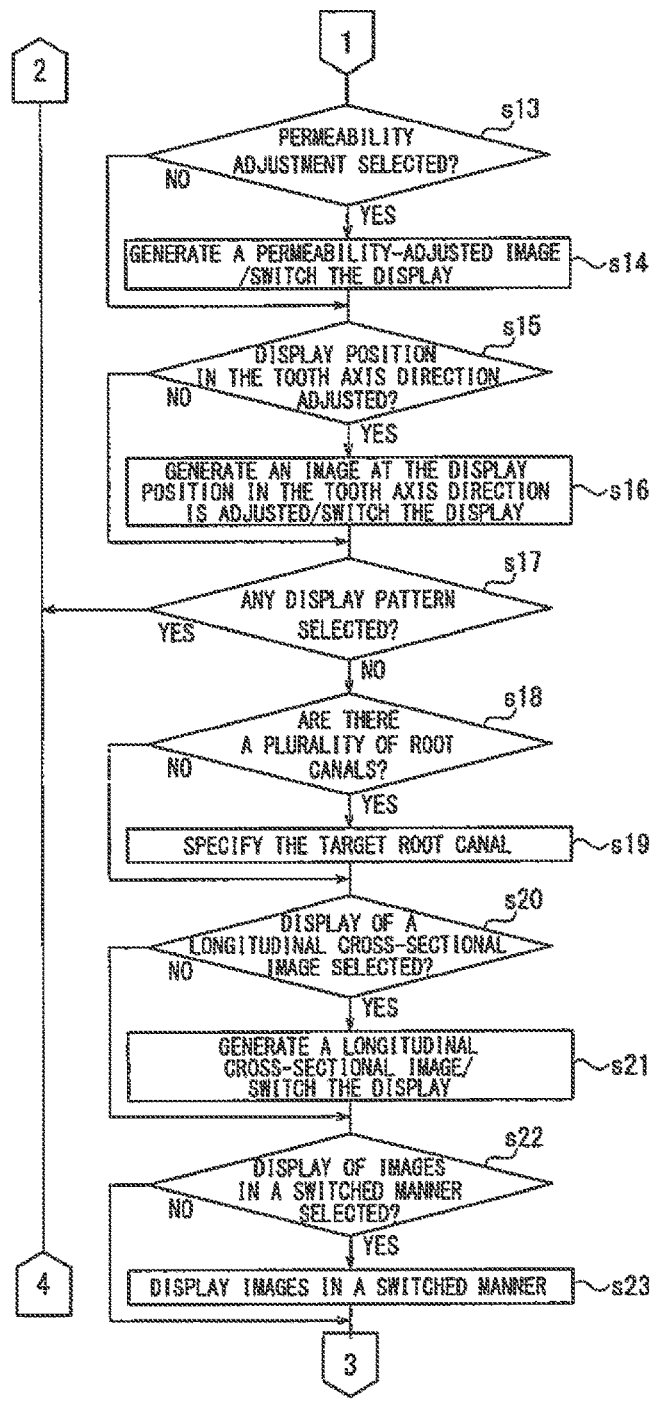
FIG. 9 is a flowchart showing the dental care process.
Figure 10:
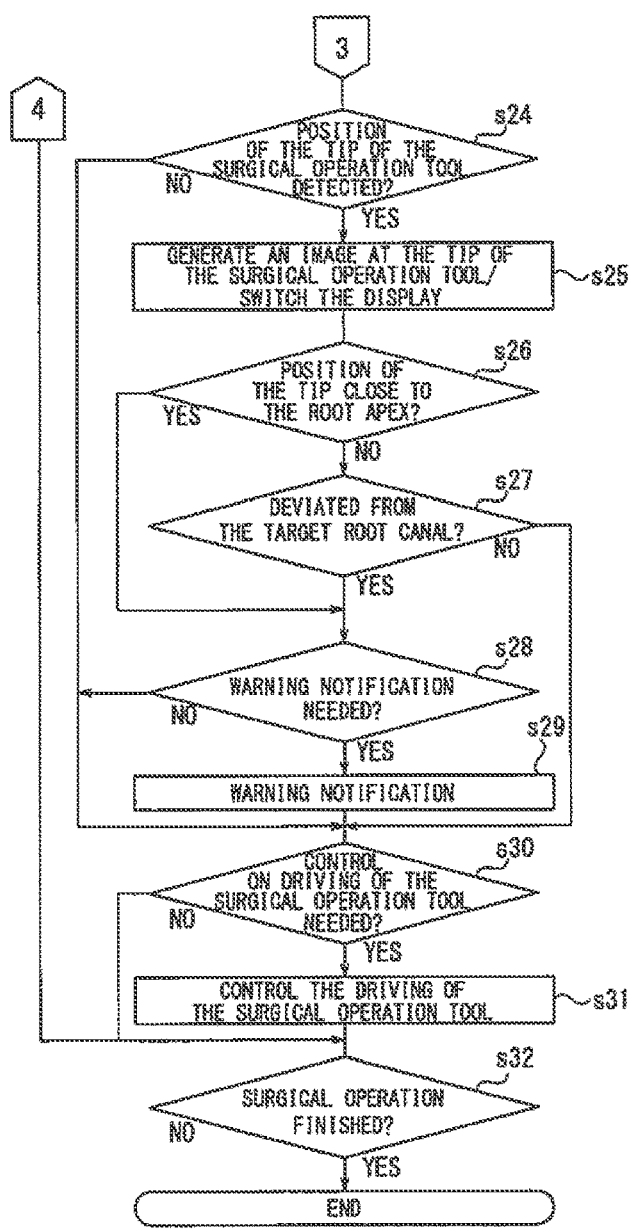
FIG. 10 is a flowchart showing the dental care process.
Figure 11A:
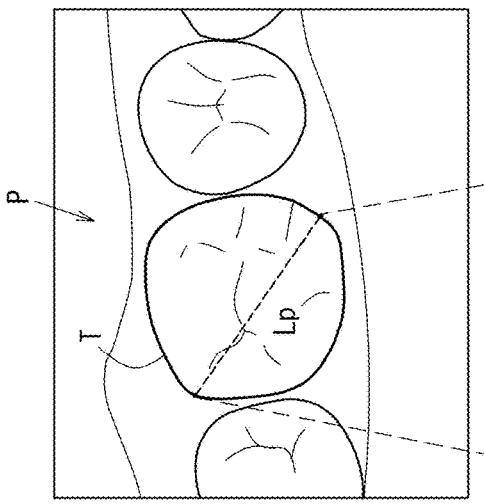
FIGS. 11A, 11B, and 11C show a method for adjusting a converted two-dimensional image.
Figure 11B:
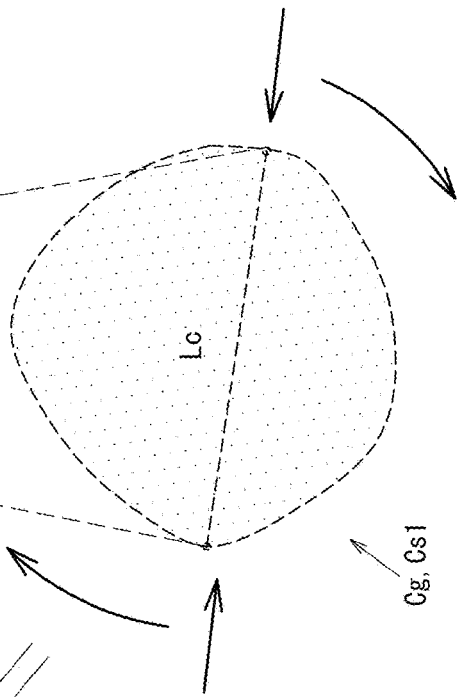
Figure 11C:
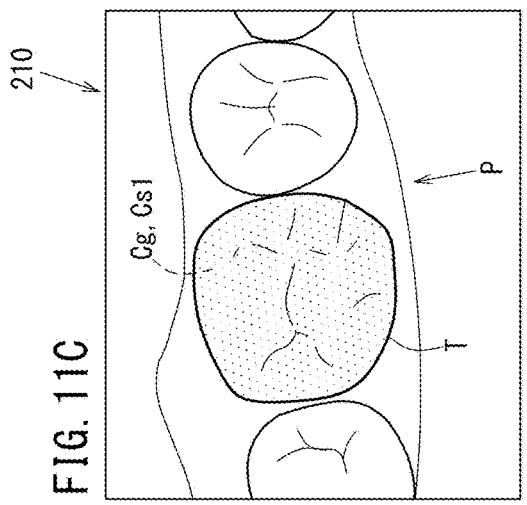
Figure 12:
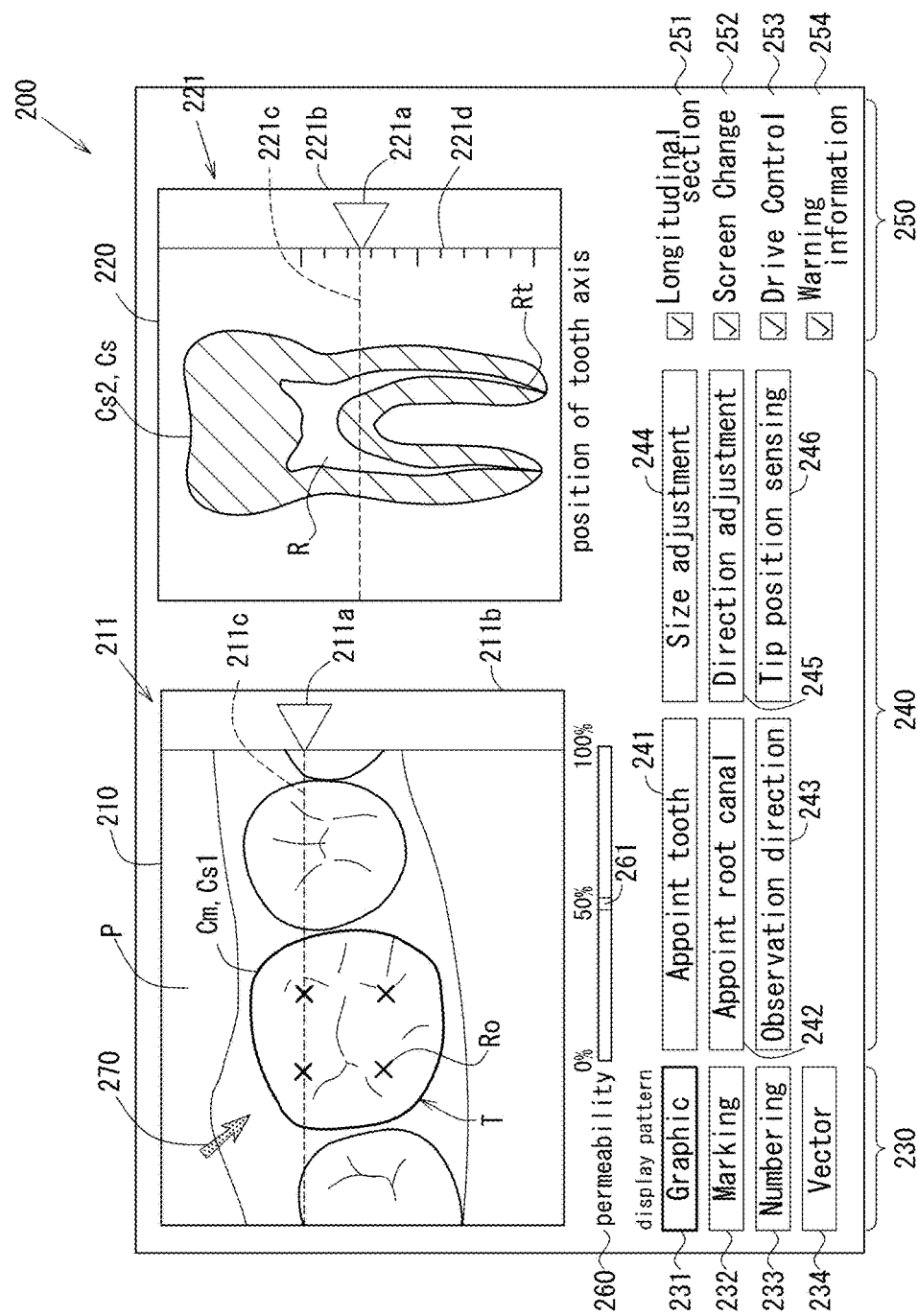
FIG. 12 shows marking overlapping display.
Figure 14A:
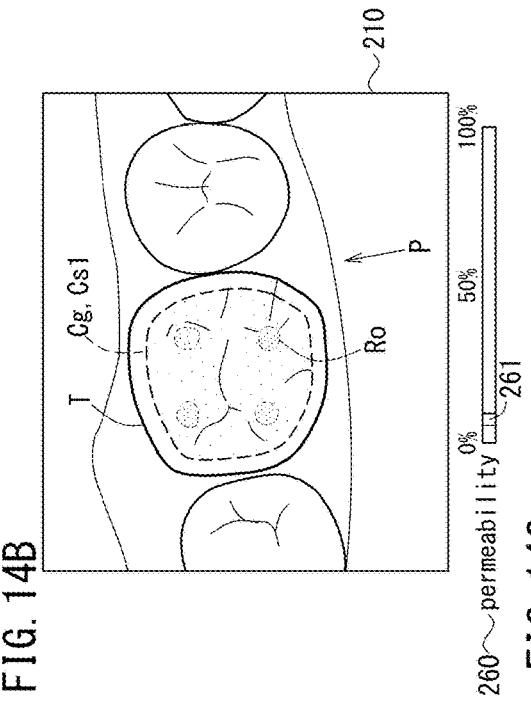
FIGS. 14A, 14B, and 14C show a method for adjusting permeability.
Figure 14B:
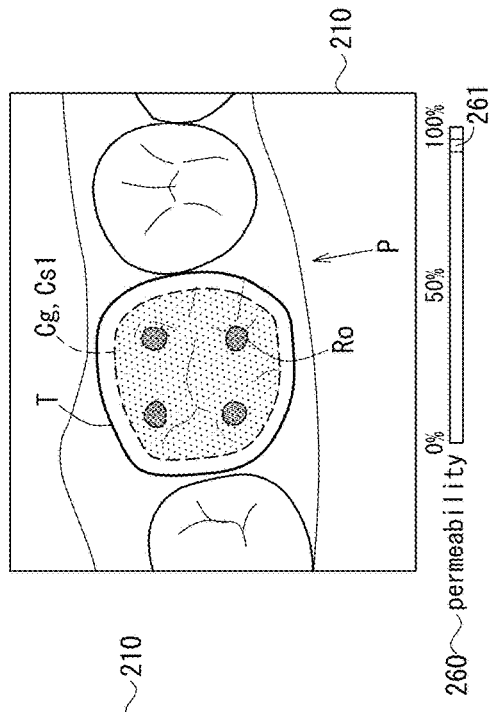
Figure 14C:
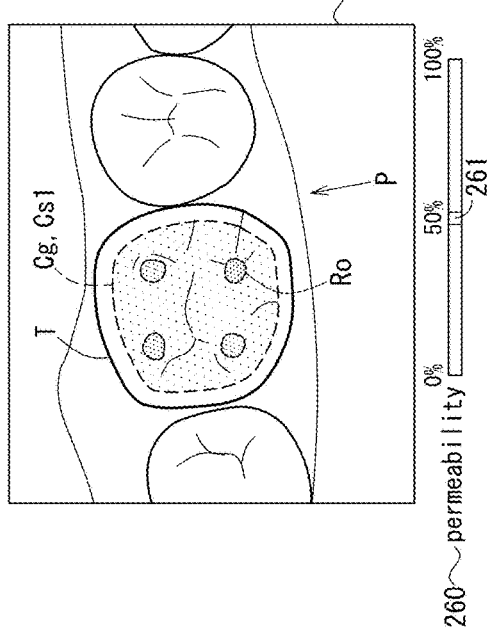

FIG. 8 through FIG. 10 are flowcharts showing a dental care process. FIGS. 11A, 11B, and 11C show a method for adjusting a converted two-dimensional image. FIG. 12 shows marking overlapping display. FIGS. 13A, 13B, 13C, and 13D show overlapping display patterns. FIGS. 14A, 14B, and 14C show a method for adjusting permeability. FIGS. 15A and 15B provide photographs showing overlapping display.

Figure 18B:
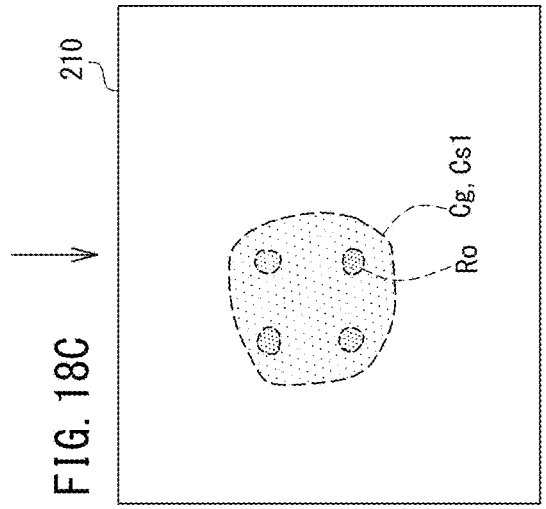
FIGS. 18A, 18B, and 18C show switching of displays.
Figure 18C:
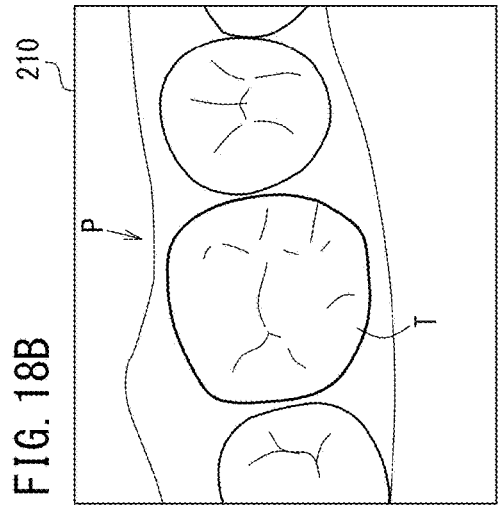
Figure 18A:
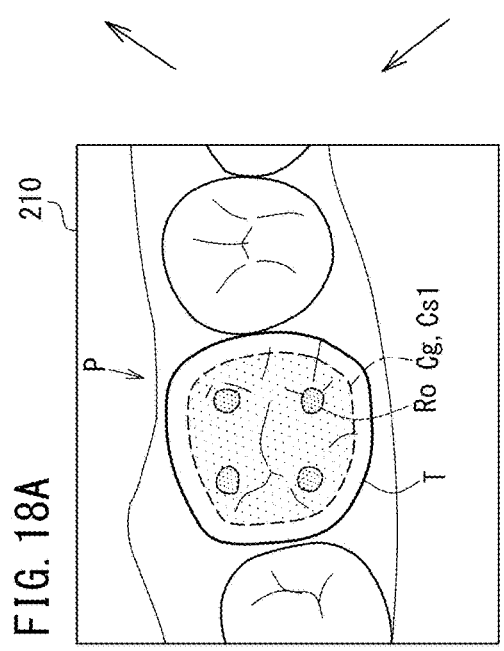
Figure 20:
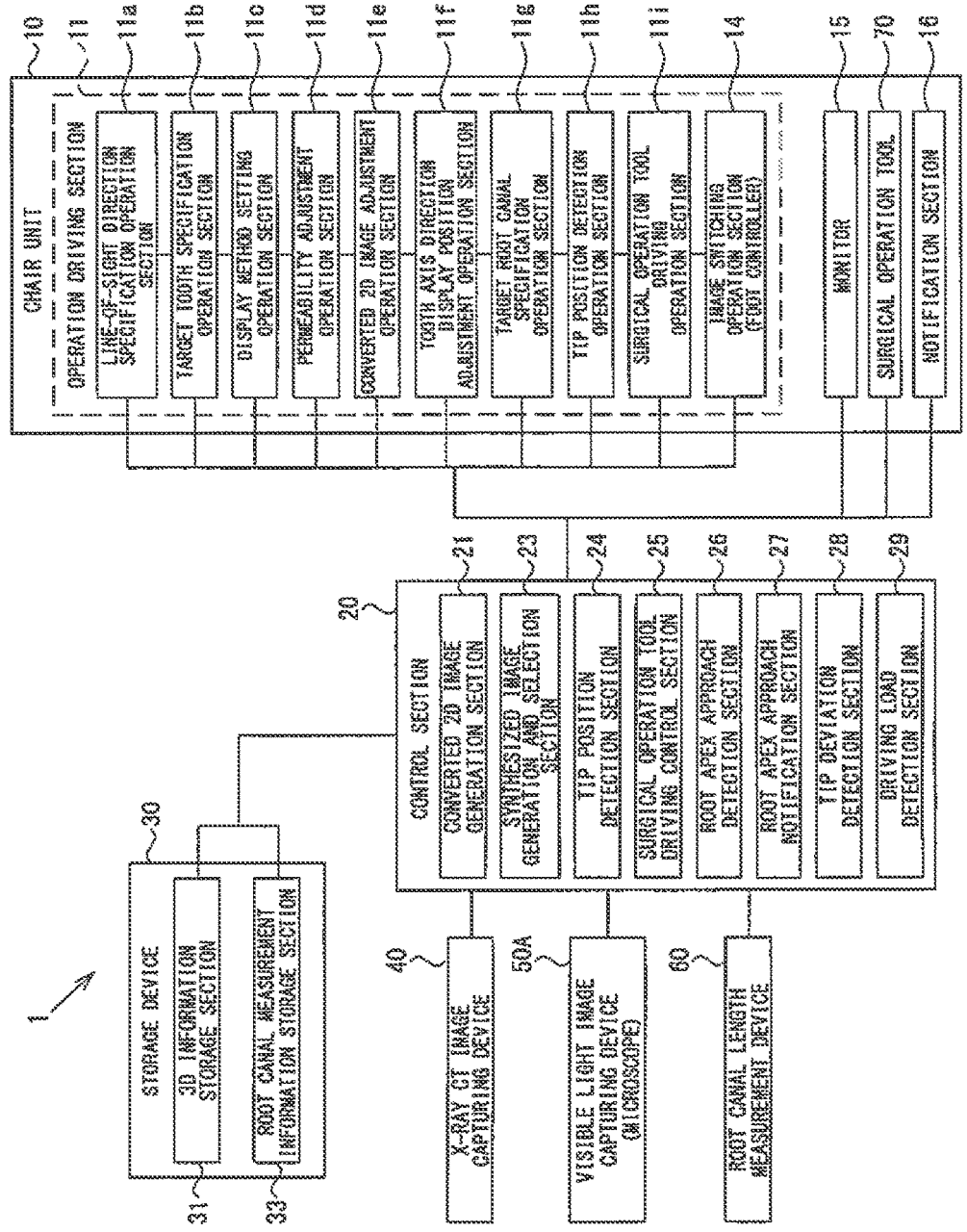
FIG. 20 is a block diagram of a medical care system in another form.
Figure 21:
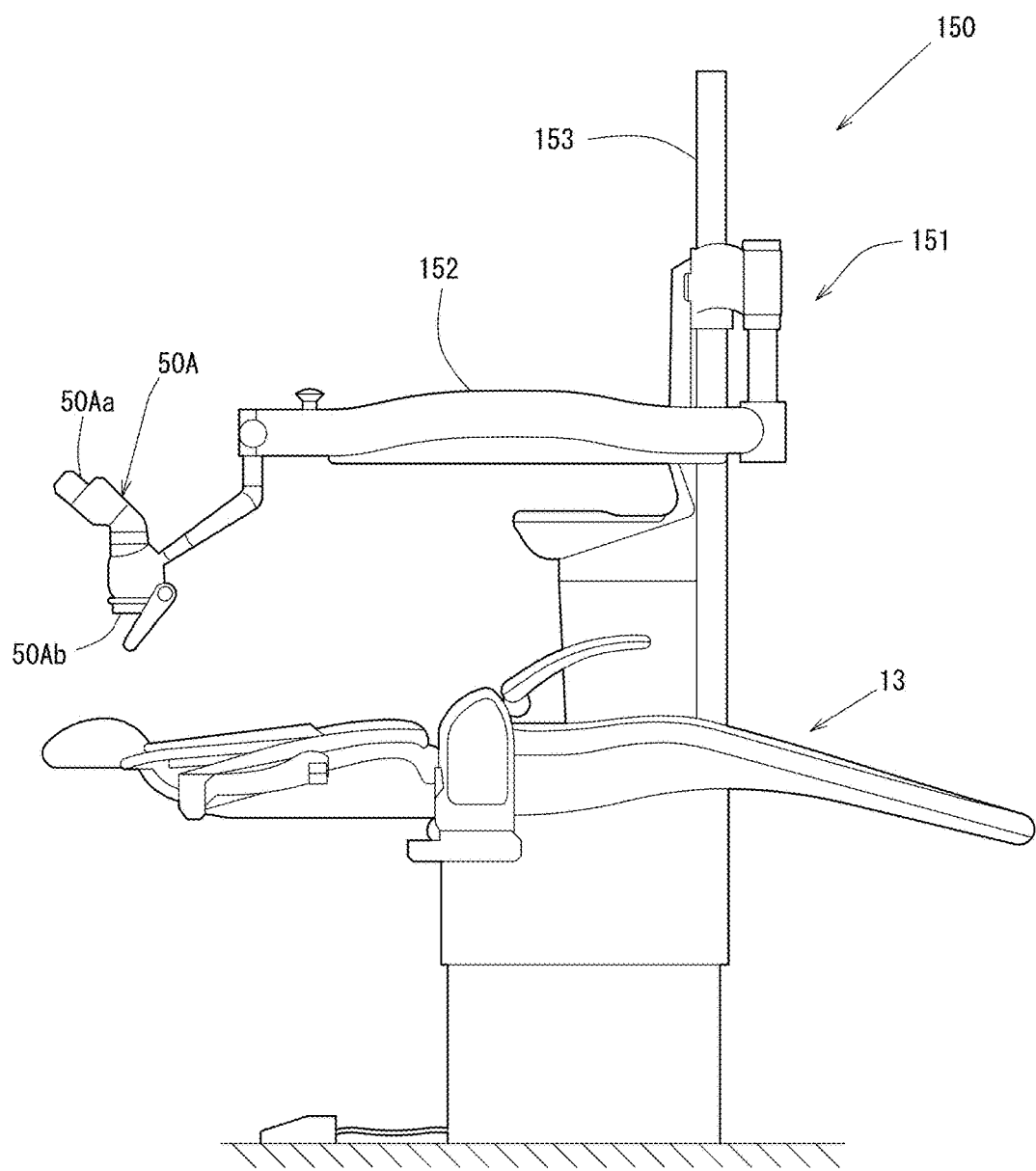
FIG. 21 is a schematic view of a microscope-inclusive dental care instrument.

FIG. 16 shows a display position adjustment scroll bar 221 on the image overlapping display screen 200. FIGS. 17A, 17B, 17C, and 17D show display position adjustment in a tooth axis direction. FIGS. 18A, 18B, and 18C show switching of displays. FIG. 19 shows display of a tip of the surgical operation tool 70 on the image overlapping display screen 200. FIG. 20 is a block diagram of the medical care system 1 in the case where a microscope main body 50A is used as a visible light image capturing device. FIG. 21 is a schematic view of the chair unit 10 equipped with the microscope main body 50A (dental care instrument 150).

The medical care system 1 includes the chair unit 10, a control section 20, a storage device 30, the X-ray CT image capturing device 40, the intraoral camera 50 acting as a visible light image capturing device, and the root canal length measurement device 60.

The control section 20 includes a CPU, a ROM and a RAM and has the functional elements described below in detail. The control section 20 includes a converted 2D image generation section 21 that converts three-dimensional information acquired by the X-ray CT image capturing device 40 into a two-dimensional image of a prescribed plane to generate a converted two-dimensional image Cs (hereinafter, referred to as a "converted 2D image Cs"), a 2D image generation section 22 that generates a 2D captured image P based on information captured by the intraoral camera 50, a synthesized image generation and selection section 23 that generates a synthesized image by synthesizing an articulation face direction converted 2D image Cs1, among converted 2D images Cs generated by the converted 2D image generation section 21, and the 2D captured image P generated by the 2D image generation section 22, a tip position detection section 24 that detects a position of a tip of the surgical operation tool 70 described later, a surgical operation tool driving control section 25 that controls the driving of the surgical operation tool 70, a root apex approach detection section 26 that detects that the tip of the surgical operation tool 70 has approached a root apex, a root apex approach notification section 27 that notifies the approach of the surgical operation tool 70 to the root apex detected by the root apex approach detection section 26, a tip deviation detection section 28 that detects that the tip of the surgical operation tool 70 has deviated from a root canal R, and a driving load detection section 29 that detects a driving load on the surgical operation tool 70.

The tip position detection section 24 may detect the position of the tip by use of a conventional detection method. For example, a three-dimensional position measurement marker detectable by an infrared detector or a magnetic sensor detectable by a three-dimensional magnetic detector may be attached to a root canal treating hand piece 70a described later, so that the position of a shaft 72a of a cutting tool 72 of the root canal treating hand piece 70a can be estimated.

The storage device 30 includes an HDD, an SSD or the like, and has the following functional elements. The storage device 30 includes a 3D information storage section 31 that stores three-dimensional information (hereinafter, referred to as "3D information") acquired by the X-ray CT image capturing device 40, a 2D image information storage section 32 that stores two-dimensional image information (hereinafter, referred to as "2D image information") captured by the intraoral camera 50, and a root canal measurement information storage section 33 that stores root canal measurement information such as, for example, a root canal length measured by the root canal length measurement device 60.

As shown in FIG. 2, the chair unit 10 includes an operation driving section 11, a base unit 12 including a suction device that sucks saliva, cooled water or the like and a device usable to gargle, a medical care chair 13 including a reclining back sheet and an up/down movable seat, a foot controller 14 connected to the medical care chair 13 and including a pedal 14a which is operable by a foot of an operator and can detect that the pedal 14a has been stepped on and also can detect the amount of stepping, a monitor 15, a notification section 16, and the surgical operation tool 70 (a plurality of the surgical operation tools 70 are shown in FIG. 2).

As shown in FIG. 2, the operation driving section 11 includes various types of operation devices 112 located in a tray table 111 provided on a top surface of the operation driving section 11, the surgical operation tools 70 attachable to a holder provided forward to the various types of operation devices 112, a driving section (not shown) that drives the surgical operation tools 70, and the monitor 15 provided on a back side of the operation driving section 11.

The various types of devices 112 include a touch screen, a pointing stick, a switch and the like. The various types of devices 112 may include an optional input device such as a mouse or the like.

The operation driving section 11 includes, other than the foot controller 14 acting as an image switching/parallel display operation section, the following functional elements: a line-of-sight direction specification operation section 11a, a target tooth specification operation section 11b, a display method setting operation section 11c, a permeability adjustment operation section 11d, a converted 2D image adjustment operation section 11e, a tooth axis direction display position adjustment operation section 11f, a target root canal specification operation section 11g, a tip position detection operation section 11h, and a surgical operation tool driving operation section 11i.

The line-of-sight direction specification operation section 11a specifies an image capturing direction in which a tooth T has been captured by the intraoral camera 50 or the microscope main body 50A described below (see FIG. 21).

The target tooth specification operation section 11b specifies a tooth T which is a target of surgical operation from the 2D captured image P captured by the intraoral camera 50 or the microscope main body 50A (see FIG. 21), and extracts 3D information on the corresponding tooth T from a plurality of pieces of 3D information stored on the 3D information storage section 31.

The display method setting operation section 11c selects and sets a display pattern with which the articulation face direction converted 2D image Cs1 is to be displayed on the image overlapping display screen 200 described later.

The permeability adjustment operation section 11d adjusts the permeability of the articulation face direction converted 2D image Cs1 which is to be displayed as overlapping the 2D captured image P on the image overlapping display screen 200.

The converted 2D image adjustment operation section 11e adjusts the size and the direction of the articulation face direction converted 2D image Cs1, converted from the 3D information acquired by the X-ray CT image capturing device 40, with respect to the 2D captured image P captured by the intraoral camera 50 or the microscope main body 50A.

The tooth axis direction display position adjustment operation section 11f sets a desired depth in the tooth axis direction at which the articulation face direction converted 2D image Cs1 is to be displayed as overlapping the 2D captured image P on the image overlapping display screen 200.

The target root canal specification operation section 11g specifies a root canal R which is a surgical operation target from the articulation face direction converted 2D image Cs1 captured by the intraoral camera 50 or the microscope main body 50A, and reads 3D information on the corresponding root canal R based on the 3D information on the tooth T specified by the target tooth specification operation section 11b and extracted from the 3D information storage section 31.

The tip position detection operation section 11h instructs detection of the position of the tip of the surgical operation tool 70 to be used to perform a surgical operation on the tooth T.

The surgical operation tool driving operation section 11i, for example, performs ON/OFF switching of, or adjustment of the output of, the surgical operation tool 70 described later.

The foot controller 14 acting as the image switching/parallel display operation section performs the switching or the parallel display operation in order to display the 2D captured image P and the articulation face direction converted 2D image Cs1 in a switched manner or concurrently side by side on the image overlapping display screen 200.

An input to such operation sections (operation sections 11a through 11i) is made by use of the image overlapping display screen 200 displayed on the monitor 15 or by use of any of the various types of operation devices 112.

The notification section 16 is controlled by the root apex approach notification section 27 to make a notification by use of a sound such as a buzzer or illumination.

As shown in FIG. 3, the X-ray CT image capturing device 40 is accommodated in a hollow parallelepiped X-ray-proof chamber 40a longer in a height direction, and executes CT image capturing to collect projection data. The X-ray CT image capturing device 40 includes a revolving arm 41 which supports an X-ray generation section 41a and an X-ray detection section 41b and is movable up and down along a support pillar and revolvable. The X-ray generation section 41a emits an X-ray cone beam formed of an X-ray flux toward a surgical operation subject M1, and the X-ray detection section 41b detects the X-ray emitted by the X-ray generation section 41a.

The X-ray CT image capturing device 40 having such a structure acts as follows. The surgical operation subject M1 is located as being held between the X-ray generation section 41a and the X-ray detection section 41b supported by the revolving arm 41. While the revolving arm 41 revolves around the surgical operation subject M1, the X-ray cone beam emitted by the X-ray generation section 41a and transmitted through the surgical operation subject M1 is detected by the X-ray detection section 41b. Thus, the 3D information is acquired.

The X-ray CT image capturing device 40 is connected to the storage device 30 via the control section 20, and thus the 3D information acquired by the X-ray CT image capturing device 40 is stored on the 3D information storage section 31 of the storage device 30.

As shown in FIG. 4, the intraoral camera 50 acting as an example of visible light image capturing device directs illumination light from a tip thereof inserted into the oral cavity of the surgical operation subject M1 toward an image capturing target site, which is an area of interest, and receives the light reflected by the image capturing target site by a solid-state image capturing sensor (not shown) such as a CMOS or the like to capture the 2D captured image P.

The intraoral camera 50 is connected to the storage device 30 via the control section 20, and thus the 2D captured image P captured by the intraoral camera 50 is stored on the 2D image information storage section 32 of the storage device 30.

As shown in FIG. 5, the root canal length measurement device 60 that measures the position of the root apex Rt, which is a tip of the root canal R of the tooth T, by an electric current value includes a device main body 61 including an operation section below a liquid crystal display section, a file electrode cord 63 connected to the device main body 61 and having, at a tip thereof, a file electrode 63a that allows a file reamer 62 to be attached thereto in a conductive manner, and an oral cavity electrode cord 64 having, at a tip thereof, a hook-shaped oral cavity electrode 64a which can be hooked at a corner of the mouth of the surgical operation subject M1.

The root canal length measurement device 60 having such a structure acts as follows. The oral cavity electrode 64a is hooked at a corner of the surgical operation subject M1, and the file reamer 62 is inserted into the root canal R of the tooth T. A position with respect to the root apex Rt of the root canal R of the tooth T can be measured based on an electric current value.

The root canal length measurement device 60 is connected to the storage device 30 via an appropriate communication unit (not shown), and thus the result of the measurement performed by the root canal length measurement device 60 is stored on the root canal measurement information storage section 33 of the storage device 30.

As shown in FIG. 6, the root canal treating hand piece 70a acting as the surgical operation tool 70 has a micromotor, a control section, and a root canal length measurement section built in a hand piece main body 71, and has a replaceable rotatable cutting tool 72 provided at a tip thereof. The root canal treating hand piece 70a is connected to the oral cavity electrode (not shown) via a rear-side connection cable (not shown). The communication to the chair unit 10 may be performed by use of a cable (not shown) or wirelessly.

The root canal treating hand piece 70a having such a structure acts as follows. The root canal treating hand piece 70a is driven by the surgical operation tool driving operation section 11i via the control section built in the hand piece main body 71 to cut off a decayed part or a contaminated root canal wall of the tooth T as the surgical operation target.

With reference to FIG. 7, the image overlapping display screen 200 displayed on the monitor 15 of the medical care system 1 having such a structure will be described.

The image overlapping display screen 200 displayed on the monitor 15 includes an articulation face direction 2D image display section 210 located in upper left part, a cross-sectional image display section 220 located in an upper right part, a display pattern selection section 230 located in a lower left part, various types of selection operation sections 240 located in a lower central part, a command check box section 250 located in a lower right part, a permeability adjustment scroll bar 260 displayed between the articulation face direction 2D image display section 210 and the display pattern selection section 230 and acting as the permeability adjustment operation section 11d, and a cursor 270 operable by the pointing device among the various types of operation devices 112 (when operated by the mouth, occasionally referred to as a "mouse pointer" or simply as a "pointer").

The articulation face direction 2D image display section 210 displays, in an overlapping manner, the 2D captured image P captured by the intraoral camera 50 or the microscope main body 50A (see FIG. 21) and stored on the 2D image information storage section 32, and the articulation face direction converted 2D image Cs1, in a display pattern selected by the display pattern selection section 230. The articulation face direction 2D image display section 210 also displays these images as a synthesized image. The articulation face direction 2D image display section 210 includes a cross-sectional position adjustment scroll bar 211 that accepts an operation of making a setting such that a converted 2D cross-sectional image Cs2 to be displayed in the cross-sectional image display section 220 is of a desired position of the tooth T. The cross-section at the position specified by the cross-sectional position adjustment scroll bar 211 is an example of a predetermined plane. (Hereinafter, the position of the tooth T at which the converted 2D cross-sectional image Cs2 is displayed in the cross-sectional image display section 220 will be referred to as a "cross-sectional position".)

This will be described in more detail. A knob 211a in an arrow 211b of the cross-sectional position adjustment scroll bar 211 is operated by the cursor 270 to set the cross-sectional position of the tooth T at which the converted 2D cross-sectional image Cs2 is to be displayed in the cross-sectional image display section 220. The knob 211a provides a cross-section display line 211c, which specifies such a cross-sectional position.

The cross-sectional position can be set by holding and moving the cross-section display line 211c to a desired position by a so-called drag-and-drop operation made on the cursor 270. The arrow 211b and the knob 211a may be omitted, so that the cross-section display line 211c is directly held and moved (see FIG. 24, 211cX).

The cross-sectional image display section 220 displays the converted 2D cross-sectional image Cs2 at the cross-sectional position, specified by the cross-section display line 211c, of the tooth T which is set by the target tooth specification operation section 11b shown in FIG. 1. In addition, the cross-sectional image display section 220 includes the display position adjustment scroll bar 221 that accepts an operation of making a setting such that the articulation face direction converted 2D image Cs1 to be displayed in the articulation face direction 2D image display section 210 is of a desired position of the converted 2D cross-sectional image Cs2 in the tooth axis direction. (Hereinafter, the position of the tooth T in the tooth axis direction at which the articulation face direction converted 2D image Cs1 is displayed in the articulation face direction 2D image display section 210 will be referred to as a "display position" or "cross-section display position".)

The display position adjustment scroll bar 221 sets, by use of a knob 221a, a desired cross-section display position of the tooth T in the tooth axis direction at which the articulation face direction converted 2D image Cs1 is to be displayed in the articulation face direction 2D image display section 210. Thus, the display position adjustment scroll bar 221 acts as the tooth axis direction display position adjustment operation section 11f.

This will be described in more detail. The knob 221a in an arrow 221b of the display position adjustment scroll bar 221 is operated by the cursor 270 to set the display position of the tooth T in the tooth axis direction at which the articulation face direction converted 2D image Cs1 is to be displayed in the articulation face direction 2D image display section 210. The knob 221a provides a cross-section display line 221c, which specifies such a display position. As shown in FIG. 7, the cross-section display line 221c is in the vicinity of the center in the tooth axis direction, namely, in a top part of the root canal R, in a default setting.

The cross-sectional image display section 220 also includes a scale 221d along the arrow 221b. The scale 221d shows a distance from the cross-section display line 221c to the root apex Rt. The arrow 221b and the knob 221a may be omitted, so that the cross-section display line 221c is directly held and moved, like in the case of the cross-sectional position adjustment scroll bar 211.

The converted 2D cross-sectional image Cs2 displayed in the cross-sectional image display section 220 is generated based on the 3D information, acquired by the X-ray CT image capturing device 40, on the tooth T set by the target tooth specification operation section 11b shown in FIG. 1.

As an image of a cross-section along the tooth axis direction which is to be displayed in the cross-sectional image display section 220, the converted 2D cross-sectional image Cs2 is generated as follows. The 3D information of the tooth T which is stored on the 3D information storage section 31 of the storage device 30 is read and converted by the converted 2D image generation section 21 such that the resultant converted 2D cross-sectional image Cs2 is of the cross-section specified by the cursor 270 in the articulation face direction 2D image display section 210 (the cross-section shown in FIG. 7 passes the root canal R).

In FIG. 7, the converted 2D cross-sectional image Cs2 is of a the cross-section of the tooth T that is specified by the cross-section display line 211c displayed in the articulation face direction 2D image display section 210. The converted 2D cross-sectional image Cs2 is generated by the converted 2D image generation section 21 based on the 3D information stored on the 3D information storage section 31 and is displayed in the cross-sectional image display section 220.

The articulation face direction converted 2D image Cs1 is of a cross-section which is parallel to an articulation face and is specified by the cross-section display line 221c. The articulation face direction converted 2D image Cs1 is generated by the converted 2D image generation section 21 based on the 3D information stored on the 3D information storage section 31 and is displayed as overlapping the 2D captured image P in the articulation face direction 2D image display section 210. The display is made after the articulation face direction converted 2D image Cs1 is positionally adjusted to the 2D captured image P. Herein, the expression "positionally adjust" specifically encompasses rotation, magnification adjustment and positional adjustment of the image.

The display pattern selection section 230 acts as the display method setting operation section 11c. For example, the display pattern selection section 230 includes various types of selection sections formed of a touch panel. In more detail, the display pattern selection section 230 includes a graphic selection section 231, a marking selection section 232, a numbering selection section 233, and a vector selection section 234. The graphic selection section 231 provides graphic display of the articulation face direction converted 2D image Cs1, to be displayed in the articulation face direction 2D image display section 210 in an overlapping manner, as a converted 2D permeable image Cg. Referring to FIG. 12 and FIG. 13B, the marking selection section 232 displays a converted 2D marking image Cm in which the positions of root canal orifices Ro are represented by "x". In the case where there are a plurality of root canal orifices Ro, the numbering selection section 233 displays a converted 2D numbering image Cn (see FIG. 13C) in which the plurality of root canal orifices are represented by numbers. The vector selection section 234 displays a converted 2D arrow image Cv (see FIG. 13D) in which the directions of the root canals R are represented by arrows. In the display pattern section 230, the graphic selection section 231 is checked in a default setting.

The various types of selection operation sections 240 include an appoint tooth selection section 241, an appoint root canal selection section 242, an observation direction selection section 243, a size adjustment selection section 244, a direction adjustment selection section 245, and a tip position sensing selection section 246. In the example of FIG. 7, the selection sections are each formed of a touch screen provided in the liquid crystal display section. Alternatively, the selection sections may be formed of hardware such as a pushbutton switch or the like.

The appoint tooth selection section 241 acts as the target tooth specification operation section 11b. After an operation is made on the appoint tooth selection section 241, the tooth T which is the surgical operation target is specified from the 2D captured image P displayed in the articulation face direction 2D image display section 210. The specification is made by the cursor 270 through an operation made on the pointing device among the various types of operation devices 112. Thus, the tooth T which is the surgical operation target is set among a plurality of teeth T captured in the 2D captured image P.

The appoint root canal selection section 242 acts as the target root canal specification operation section 11g. After an operation is made on the appoint root canal selection section 242, the root canal orifice Ro which is a surgical operation target is specified from the articulation face direction converted 2D image Cs1 displayed in the articulation face direction 2D image display section 210 in an overlapping manner. The specification is made by the cursor 270 through an operation made on the pointing device among the various types of operation devices 112. Thus, the root canal orifice Ro which is the surgical operation target is set among the plurality of root canal orifices Re displayed in the articulation face direction converted 2D image Cs1.

The observation direction selection section 243 acts as the line-of-sight direction specification operation section 11a, and is an instruction and selection section that adjusts the image capturing angle of the intraoral camera 50 that captures the tooth T, namely, the line-of-sight direction for capturing the 2D captured image P. Without an instruction to adjust the image capturing angle, a line-of-sight direction in which a plane generally parallel to the articulation face is captured, namely, a line-of-sight direction along the tooth axis direction is selected in a default setting.

The size adjustment selection section 244 acts as the converted 2D image adjustment operation section 11e together with the direction adjustment selection section 245 described later. The size adjustment selection section 244 is an instruction section used to adjust the size of the articulation face direction converted 2D image Cs1, of the tooth T specified as the target tooth, generated by the converted 2D image generation section 21 based on the 3D information extracted from the 3D information storage section 31. The size adjustment is performed with respect to the size of the tooth T to be displayed in the 2D captured image P in the articulation face direction 2D image display section 210.

The direction adjustment selection section 245 acts as the converted 2D image adjustment operation section 11e together with the size adjustment selection section 244. The direction adjustment selection section 245 is an instruction section used to adjust the direction of the articulation face direction converted 2D image Cs1, of the tooth T specified as the target tooth, generated by the converted 2D image generation section 21 based on the 3D information extracted from the 3D information storage section 31. The direction adjustment is performed with respect to the direction of the tooth T to be displayed in the 2D captured image P in the articulation face direction 2D image display section 210.

The tip position sensing section 246 acts as the tip position detection operation section 11h, and is an instruction section used to detect the position of the tip of the surgical operation tool 70 during the surgical operation performed on the tooth T.

The command check box section 250 includes a longitudinal section check box 251, a screen change check box 252, a drive control check box 253, and a warning information check box 254.

The longitudinal section check box 251 is to be checked for displaying the cross-sectional image display section 220.

The screen change check box 252 to be checked for displaying the 2D captured image P and the articulation face direction converted 2D image Cs1 in a switched manner in the articulation face direction 2D image display section 210 by an operation of stepping on the foot controller 14.

The drive control check box 253 is to be checked for restricting the driving of the surgical operation tool 70 when, for example, an excessive load has been put on the surgical operation tool 70 or when the tip of the surgical operation tool 70 has approached the root apex Rt.

The warning information check box 254 is to be checked so that it is notified when the tip of the surgical operation tool 70 approaches the root apex Rt.

The permeability adjustment scroll bar 260 acts as the permeability adjustment operation section 11d. A knob 261 of the permeability adjustment scroll bar 260 is dragged by the cursor 270 to set the permeability of the articulation face direction converted 2D image Cs1 to be displayed in the articulation face direction 2D image display section 210. In the permeability adjustment scroll bar 260, the knob 261 represents 50% to provide a semi-permeable state in a default setting.

As described above, the articulation face direction converted 2D image Cs1 is displayed as overlapping the 2D captured image P on the image overlapping display screen 200 having the above-described structure. While the articulation face direction converted 2D image Cs1 is thus displayed, a medical care is performed on the root canal R of the tooth T as the surgical operation target. With reference to the flowcharts in FIG. 8 through FIG. 10, a display method and a surgical operation method used for the medical care will be described.

First, in order to perform a medical care on the root canal R of the tooth T which is the surgical operation target, the operator captures a 2D captured image P of the tooth T and the vicinity thereof by the X-ray CT image capturing device 40 (step s1).

In this step, the 2D captured image P captured by the X-ray CT image capturing device 40 is stored on the 2D image information storage section 32 of the storage device 30 via the control section 20, and is also displayed in the articulation face direction 2D image display section 210 on the image overlapping display screen 200.

On the 2D captured image P displayed in the articulation face direction 2D image display section 210, the appoint tooth selection section 241 acting as the target tooth specification operation section 11b is operated, and the target tooth T is specified by the cursor 270 (step s2). Then, the observation direction selection section 243 acting as the line-of-sight direction specification operation section 11a is operated to specify the line-of-sight direction of the X-ray CT image capturing device 40 (step s3). When this occurs, the control section 20 extracts the 3D information on the corresponding tooth T from the 3D information stored on the 3D information storage section 31 of the storage device 30 (step s4), generates the articulation face direction converted 2D image Cs1 in the specified line-of-sight direction by the converted 2D image generation section 21 (step s5), and provisionally displays the articulation face direction converted 2D image Cs1 in the articulation face direction 2D image display section 210.

As described above, when the line-of-sight direction is not specified in step s3, the tooth axis direction in which the root canal orifice Ro is observed most easily is set as the default of the line-of-sight direction. Therefore, the articulation face direction converted 2D image Cs1 is generated in a plane parallel to the articulation face.

In the case where the position of the articulation face direction converted 2D image Cs1 provisionally displayed in the articulation face direction 2D image display section 210 is different from the position of the tooth T specified in the 2D captured image P, the articulation face direction converted 2D image Cs1 is dragged to adjust the position thereof. When the size or the direction of the articulation face direction converted 2D image Cs1 is different from that of the tooth T, the size adjustment selection section 244 or the direction adjustment selection section 245 acting as the converted 2D image adjustment operation section 11e is operated to adjust the size or the direction of the articulation face direction converted 2D image Cs1 so as to be accommodated to the tooth T in the 2D captured image P (step s6).

Now, it is assumed that, for example, as shown in FIGS. 11(a) and 11(b), the maximum diameter of the articulation face direction converted 2D image Cs1 is longer than that of the tooth T in the 2D captured image P and extends in a different direction from that of the tooth T in the 2D captured image P. In this case, line Lp representing the maximum diameter of the tooth T in the 2D captured image P is specified (see FIG. 11A), and line Lc representing the maximum diameter of the articulation face direction converted 2D image Cs1 is specified (see FIG. 11B).

Line Lc of the articulation face direction converted 2D image Cs1 is longer than line Lp of the tooth Tin the 2D captured image P, and line Lc extends in a different direction from that of line Lp in a counterclockwise direction. Therefore, the articulation face direction converted 2D image Cs1 is rotated clockwise such that the angle of line Lc of the articulation face direction converted 2D image Cs1 matches the angle of line Lp of the tooth T in the 2D captured image P (the "angle" herein is the angle with respect to the screen of the articulation face direction 2D image display section 210). In addition, the articulation face direction converted 2D image Cs1 is contracted such that the length of line Lc of the articulation face direction converted 2D image Cs1 matches the length of line Lp of the tooth T in the 2D captured image P. As a result, as shown in FIG. 11C, the articulation face direction converted 2D image Cs1 is matched to the tooth Tin the 2D captured image Pin both of the direction and the size, and thus can be displayed as overlapping the tooth T in the 2D captured image P in the articulation face direction 2D image display section 210. The position in the 2D captured image P at which the root canal R is to be present, and the position of the root canal R in the articulation face direction converted 2D image Cs1, match each other.

The size of the articulation face direction converted 2D image Cs1 may be adjusted to the size of the 2D captured image P by the following method. An area size of the tooth T in the 2D captured image P and an area size of the articulation face direction converted 2D image Cs1 are found by image analysis, and the size of the articulation face direction converted 2D image Cs1 is adjusted such that the two area sizes match each other.

The articulation face direction converted 2D image Cs1 adjusted so as to overlap the 2D captured image P is displayed in a pattern selected by the display pattern selection section 230 acting as the display method setting operation section 11c (steps s7 through s11).

This will be described in more detail. When the marking selection section 232 of the display pattern selection section 230 is operated (step s7: YES), the following is performed. The converted 2D marking image Cm in which the positions of the root canal orifices Ro in the articulation face direction converted 2D image Cs1 are represented by "x" as shown in the articulation face direction 2D image display section 210 of FIG. 12 or in FIG. 13B, and the 2D captured image P, are synthesized by the synthesized image generation and selection section 23 to generate a synthesized image. The synthesized image is displayed in the articulation face direction 2D image display section 210 (step s8). The size of "x" displayed in the converted 2D marking image Cm may be adjusted in accordance with the size of the root canal orifices Re.

When the numbering selection section 233 of the display pattern selection section 230 is operated (step s7: NO; s9: YES), the following is performed. The converted 2D numbering image Cn in which the positions of the root canal orifices in the articulation face direction converted 2D image Cs1 are represented by numbers as shown in FIG. 13C, and the 2D captured image P, are synthesized by the synthesized image generation and selection section 23 to generate a synthesized image. The synthesized image is displayed in the articulation face direction 2D image display section 210 (step s10).

When the vector selection section 234 of the display pattern selection section 230 is operated (step s9: NO; s11: YES), the following is performed. The converted 2D arrow image Cv in which the directions of the root canals R from the positions of the root canal orifices Ro in the articulation face direction converted 2D image Cs1 are represented by arrows along the articulation face direction as shown in FIG. 13D, and the 2D captured image P, are synthesized by the synthesized image generation and selection section 23 to generate a synthesized image. The synthesized image is displayed in the articulation face direction 2D image display section 210 (step s12). The length or the thickness of each arrow may be varied in accordance with the curvature of the corresponding root canal R.

When none of the marking selection section 232, the numbering selection section 233 and the vector selection section 234 is selected (step s11: NO), the converted 2D permeable image Cg specified in the default setting is displayed.

It is now assumed that either one of the converted 2D marking image Cm, the converted 2D numbering image Cn, the converted 2D arrow image Cv and the converted 2D permeable image Cg is displayed as the articulation face direction converted 2D image Cs1 as overlapping the 2D captured image P. When the permeability adjustment scroll bar 260 acting as the permeability adjustment operation section 11d is operated in this state (step s13: YES), the following is performed. The articulation face direction converted 2D image Cs1 (Cg, Cm, Cn, Cv) adjusted in terms of permeability, and the 2D captured image P, are synthesized by the synthesized image generation and selection section 23 to generate a synthesized image. The synthesized image is displayed in the articulation face direction 2D image display section 210 (step s14).

This will be described in more detail. FIGS. 14A, 14B, and 14C show permeability adjustment performed in the case where the 2D captured image P and the converted 2D permeable image Cg are displayed in an overlapping manner in the articulation face direction 2D image display section 210. As shown in FIGS. 14A, 14B, and 140, when the default permeability is 50%, the converted 2D permeable image Cg is permeable and thus the tooth T in the 2D captured image P can be visually recognized (see FIG. 14A).

In this state, the root canal orifices Ro of the converted 2D permeable image Cg can be visually recognized on the tooth T in the 2D captured image P. For example, when the knob 261 is made close to 0%, as shown in FIG. 14B, the converted 2D permeable image Cg and the root canal orifices Ro are difficult to be visually recognized. By contrast, when the knob 261 is made close to 100%, as shown in FIG. 14C, the converted 2D permeable image Cg is not permeable and thus the tooth T in the 2D captured image P is difficult to be visually recognized.

As can be seen, the knob 261 of the permeability adjustment scroll bar 260 may be slid by the cursor 270 to display the converted 2D permeable image Cg at an optional permeability. The permeability may be adjusted in accordance with, for example, the color of the tooth T in the 2D captured image P or the brightness of the captured image P such that the visibility of the root canal orifices Ro in the converted 2D permeable image Cg is improved.

As described above, the articulation face direction converted 2D image Cs1 displayed as overlapping the tooth T in the 2D captured image P is along a plane which is specified by the cross-section display line 221c of the cross-sectional image display section 220 and is parallel to the articulation face in the vicinity of the center in the tooth axis direction (up-down direction in the cross-sectional image display section 220 in FIG. 7). When the display position, in the tooth axis direction, at which the articulation face direction converted 2D image Cs1 is to be displayed is adjusted by the knob 221a (step s15: YES), the articulation face direction converted 2D image Cs1 along a plane parallel to the articulation face at the post-adjustment display position, and the 2D captured image P, are synthesized by the synthesized image generation and selection section 23 to generate a synthesized image. The synthesized image is displayed in the articulation face direction 2D image display section 210 (step s16).

This will be described in more detail. FIGS. 16, 17A, 17B, 17C, and 17D show display position adjustment in the case where the 2D captured image P and the converted 2D permeable image Cg are displayed in an overlapping manner in the articulation face direction 2D image display section 210. When the display position is lowered as shown in FIGS. 17B and 17C from the intermediate position in the default setting (see FIG. 17A), the root canal orifices Ro of the root canals R displayed in the converted 2D permeable image Cg approach the root apex Rt. The positions and the sizes of the root canal orifices Ro are changed. As can be seen, when the knob 221a is operated to continuously change the display position, the root canal orifices Ro displayed in the converted 2D permeable image Cg are changed as shown in FIG. 16 and FIG. 17D. Therefore, tracks of the root canal orifices Ro having substantially the same directivity as that of the arrows in the converted 2D arrow image Cv in which the root canals R are represented by the arrows can be displayed.

It is now assumed that the display pattern selection section 230 is further operated on the image overlapping display screen 200 in which the articulation face direction converted 2D image Cs1 is displayed as overlapping the tooth T in the 2D captured image P (step s17: YES) in the state where the adjustment of the display position of the articulation face direction converted 2D image Cs1 is finished or the display position is kept at the default position (step s13: NO). In this case, the operation is returned to step s7, and the articulation face direction converted 2D image Cs1 in accordance with the operated display pattern selection section 230 (231, 232, 233, 234) is displayed in the articulation face direction 2D image display section 210 in an overlapping manner.

It is assumed that a plurality of root canal orifices Ro are displayed in the articulation face direction converted 2D image Cs1 (step s18: YES) in the state where the display pattern of the articulation face direction converted 2D image Cs1 to be displayed as overlapping the tooth T in the 2D captured image P in the articulation face direction 2D image display section 210 is fixed in this manner (step s17: NO). In this case, the appoint root canal selection section 242 acting as the target root canal specification operation section 11g is operated to specify the root canal R which is the surgical operation target by the cursor 270 or by an input of a number among the numbers displayed in the converted 2D numbering image Cn. When this occurs, the controls section 20 sets the specified root canal R as the surgical operation target (step s19).

When the longitudinal section check box 251 is checked in the command check box 250 on the image overlapping display screen 200 (step s20: YES), the converted 2D cross-sectional image Cs2 is generated by the synthesized image generation and selection section 23 of the control section 20 based on the 3D information on the tooth T and is displayed in the cross-sectional image display section 220 (step s21). When one root canal R of the tooth T is the surgical operation target (step s18: NO), the converted 2D cross-sectional image Cs2 displayed in the cross-sectional image display section 220 is a cross-sectional view taken along a plane in the tooth axis direction passing the root canal R. Even when there are a plurality of such root canals R, the converted 2D cross-sectional image Cs2 displayed in the cross-sectional image display section 220 is a cross-sectional view taken along a plane in the tooth axis direction passing the root canal R specified in step s19.

When the longitudinal section check box 251 is not checked (step s20: NO), no converted 2D cross-sectional image Cs2 is displayed in the cross-sectional image display section 220.

It is assumed that the screen change check box 252 is checked in the command check box 250 on the image overlapping display screen 200 (step s22: YES) and the pedal 14a of the foot controller 14 is stepped on. In this case, as shown in FIGS. 18A, 18B and 18C, the display in the articulation face direction 2D image display section 210 is switched from the overlapping display of the articulation face direction converted 2D image Cs1 on the tooth T in the 2D captured image P (see FIG. 18A) to the display of only the 2D captured image P as shown in FIG. 18B, and then to the display of only the articulation face direction converted 2D image Cs1 as shown in FIG. 18C (step s23).

The order of the display of the 2D captured image P and the display of the articulation face direction converted 2D image Cs1 may be opposite to the above. Alternatively, when the pedal 14a is stepped on, the overlapping display of the articulation face direction converted 2D image Cs1 on the tooth T in the 2D captured image P may be switched to the display of only the 2D captured image P, and after this, the articulation face direction converted 2D image Cs1 and the 2D captured image P may be alternately displayed.

The display in a switched manner in steps s22 and s23 may be performed in substantially the same manner even during the surgical operation.

Figure 22:
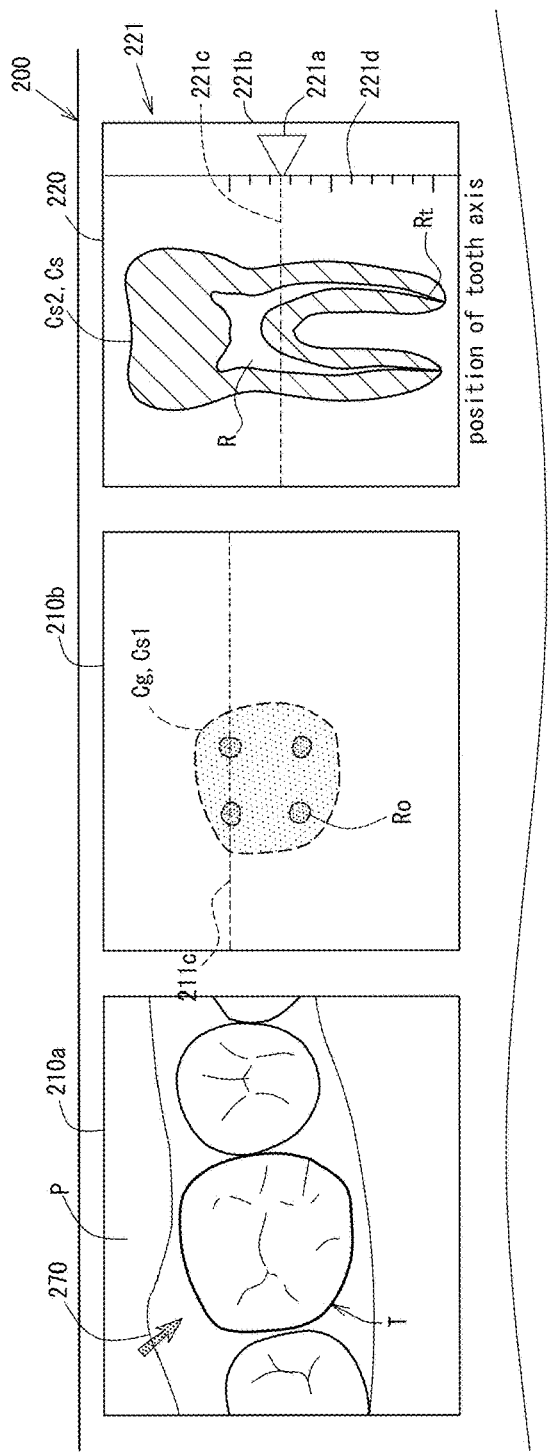
FIG. 22 shows an image overlapping display screen in another display form.

FIG. 22 shows another example of display on the image overlapping display screen 200. In this example, the 2D captured image P is displayed in an articulation face direction 2D image display section 210a while the articulation face direction converted 2D image Cs1 is displayed in an articulation face direction 2D image display section 210b separately from the 2D captured image P, instead of these images being both displayed in the articulation face direction 2D image display section 210.

Figure 23A:
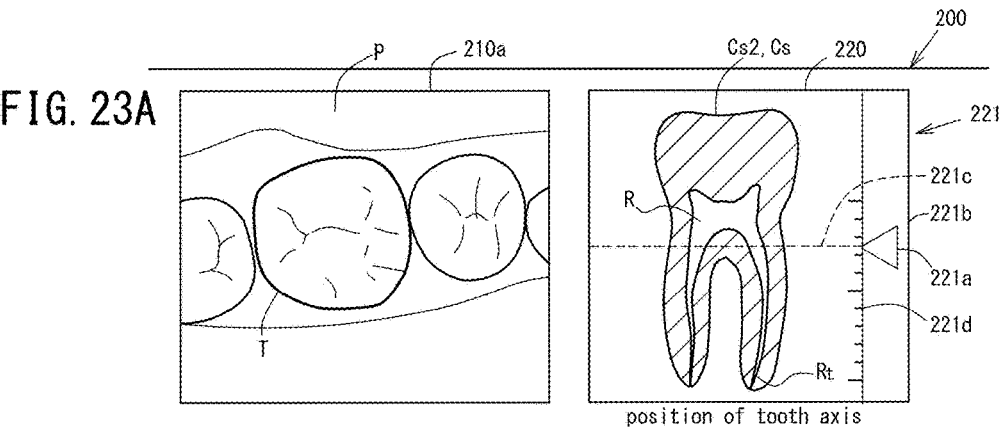
FIGS. 23A, 23B, and 23C show an image overlapping display screen in still another display form.

FIG. 23A shows still another example of display on the image overlapping display screen 200. In this example, the converted 2D cross-sectional image Cs2 in the cross-sectional image display section 220 and the 2D captured image P in the articulation face direction 2D image display section 210 are provided in one display screen side by side concurrently, instead of these images being displayed in a switched manner.

Figure 23B:
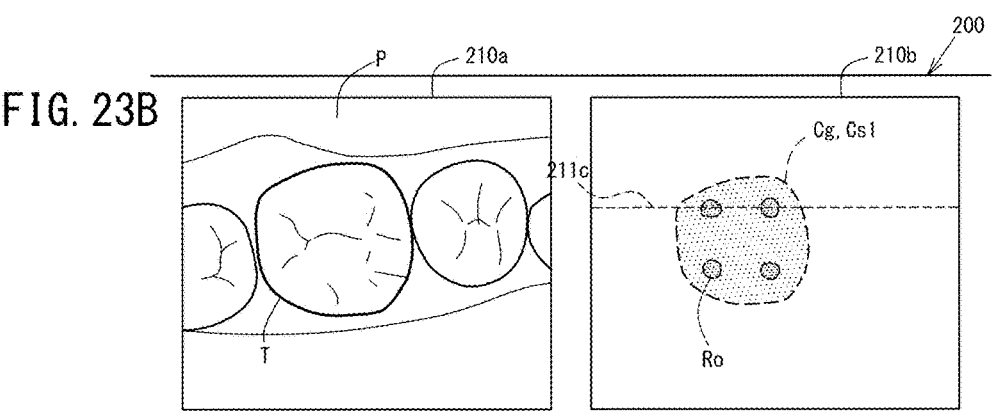
Figure 23C:
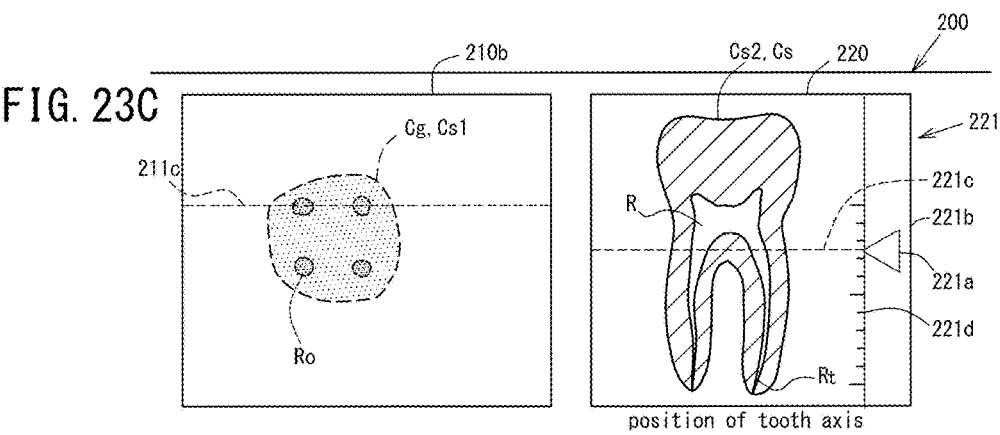

Alternatively, as shown in FIG. 23B, the 2D captured image P in the articulation face direction 2D image display section 210a and the articulation face direction converted 2D image Cs1 in the articulation face direction 2D image display section 210b may be provided in one display screen side by side concurrently. Still alternatively, as shown in FIG. 23C, the articulation face direction converted 2D image Cs1 in the articulation face direction 2D image display section 210b and the converted 2D cross-sectional image Cs2 in the cross-sectional image display section 220 may be provided in one display screen side by side concurrently. These images may be switched to each other. Such a switching operation may be performed by the foot controller 14.

The medical care is performed as follows on the root canal R specified in step s19 while the image overlapping display screen 200 is displayed on the monitor 15. First, while the root canal orifice Ro in the converted 2D permeable image Cg which is displayed as overlapping the tooth T in the 2D captured image P in the articulation face direction 2D image display section 210 on the image overlapping display screen 200 is confirmed, the tooth T is cut from an upper part thereof by the root canal treating hand piece 70a to expose the root canal orifice Ro.

In the state where the root canal orifice Ro is exposed, the root canal orifice Ro is displayed in the articulation face direction 2D image display section 210 as shown in FIGS. 15A and 15B. FIG. 15A shows that the converted 2D marking image Cm in which the root canal orifices Ro are represented by "x" is displayed as overlapping the tooth T in the 2D captured image P. FIG. 15B shows that the converted 2D numbering image Cn in which the plurality of root canal orifices Ro are numbered is displayed as overlapping the tooth T in the 2D captured image P.

The medical care on the root canal is performed as follows. A file 70b (see FIG. 19) or the root canal treating hand piece 70a are inserted from the root canal orifice Ro to remove a decayed part. Since bacteria may be even in the dentine of the root canal wall, the root canal wall is removed (expanded cutting) and the inside of the root canal R is sterilized. Then, the root canal R is filled with natural rubber called Gutta Percha, and the tooth T is crowned. Thus, the medical care on the root canal R is finished.

In such a medical care on the root canal R, the tip position sensing selection section 246 on the image overlapping display screen 200 is operated (step s24: YES), and the surgical operation tool 70 (70a, 70b) is inserted from the root canal orifice Ro to perform expanded cutting. At this point, the articulation face direction converted 2D image Cs1 in accordance with the position of the tip of the surgical operation tool 70 detected by the tip position detection section 24 is displayed in the articulation face direction 2D image display section 210 in an overlapping manner (step s25).

In the case where the converted 2D cross-sectional image Cs2 is displayed in the cross-sectional image display section 220, an illustration image of the surgical operation tool 70 may be displayed as overlapping the converted 2D cross-sectional image Cs2 in the state where the detected tip position of the surgical operation tool 70 is aligned to the converted 2D cross-sectional image Cs2. Since the scale 221d is displayed in the cross-sectional image display section 220, the distance from the tip position of the surgical operation tool 70 to the root apex Rt can be confirmed.

Now, a structure of displaying an image showing the position of a tool such as the surgical operation tool 70 or the like in the articulation face direction 2D image display section 210 in an overlapping manner will be described in detail.

Hereinafter, the file reamer 62 shown in FIG. 5, the cutting tool 72 shown in FIG. 6, the file 70b shown in FIG.

19 and the like will be each described as a "root canal treating tool RTT including a shaft TX, which is insertable into the root canal R.

The three-dimensional shape of the root canal treating tool RTT is detected and measured in advance, and is stored on, for example, the storage device 30. Therefore, the three-dimensional position or posture of the root canal treating tool RTT is detected to detect the three-dimensional position or posture of the shaft TX.

In the case where, for example, the root canal treating tool RTT is the cutting tool 72 shown in FIG. 6, the three-dimensional shape of a main body of the surgical operation tool 70 (root canal treating hand piece 70a) is detected, measured and stored in advance, and the three-dimensional shape of the cutting tool 72 is also detected, measured and stored in advance. The shaft 72a is an example of the shaft TX.

The cutting tool 72 is attached to a specific position of the main body of the root canal treating hand piece 70a. Therefore, a three-dimensional position measurement marker or the like may be attached to the main body of the root canal treating hand piece 70a as described above to monitor the three-dimensional position and the motion of the root canal treating hand piece 70a. Thus, the three-dimensional position and the motion of the shaft 72a can also be detected.

In the case where the file 72b is used independently as a cutting tool, a three-dimensional position measurement marker or the like may be directly attached to the file 72b to monitor the three-dimensional position and the motion thereof.

The three-dimensional shape of the root canal treating tool RTT is known and thus can be stored as three-dimensional image data.

The root canal treating tool RTT may be displayed as overlapping the converted 2D cross-sectional image Cs2 in the cross-sectional image display section 220. In this case, the root canal treating tool RTT may be displayed as a tool image TI which is matched to the line-of-sight direction of the converted 2D cross-sectional image Cs2 and is a two-dimensional image converted from three-dimensional image data.

When being converted into a two-dimensional image, the three-dimensional image data may be converted into, for example, an illustration image. The tool image TI does not need to show the entirety of the root canal treating tool RTT, but may show only the shaft TX or a part thereof on the tip side thereof.

When the knob 221a of the cross-sectional image display section 220 is adjusted downward in the tool axis direction in the above-described treatment state, the position of the root canal orifice Ro beyond the tip position of the surgical operation tool 70 can be displayed in the articulation face direction 2D image display section 210 as shown in FIG. 19.

It is now assumed that the root apex approach detection section 26 detects that the tip position of the surgical operation tool 70 is close to the root apex Rt based on the root canal measurement information stored on the root canal measurement storage section 33 of the storage device 30 (step s26: YES), or that the tip deviation detection section 28 detects that the tip position is not close to the root apex Rt (step s26: NO) but is deviated from the route of the root canal R specified in step s19 (step s27: YES). When the warning information check box 254 is checked in this state (step s28: YES), the notification section 16 is controlled by the root apex approach notification section 27 to make a notification (step s29).

When the drive control check box 253 is checked (step s30: YES), the surgical operation tool driving control section 25 controls the driving of the root canal treating hand piece 70a (step s31).

Even when the tip position of the surgical operation tool 70 is not detected (step s24: NO), the medical care on the root canal needs to be performed with care because the cutting tool performs cutting along the curved root canal R. Even when the drive control check box 253 is checked (step s30: YES) and the driving load detection section 29 detects that the driving load on the root canal treating hand piece 70a exceeds a prescribed load, the surgical operation tool driving control section 25 controls the driving of the root canal treating hand piece 70a (step s31).

The above-described steps are repeated until the medical care on the root canal R is finished (step s32: NO).

Figure 24:
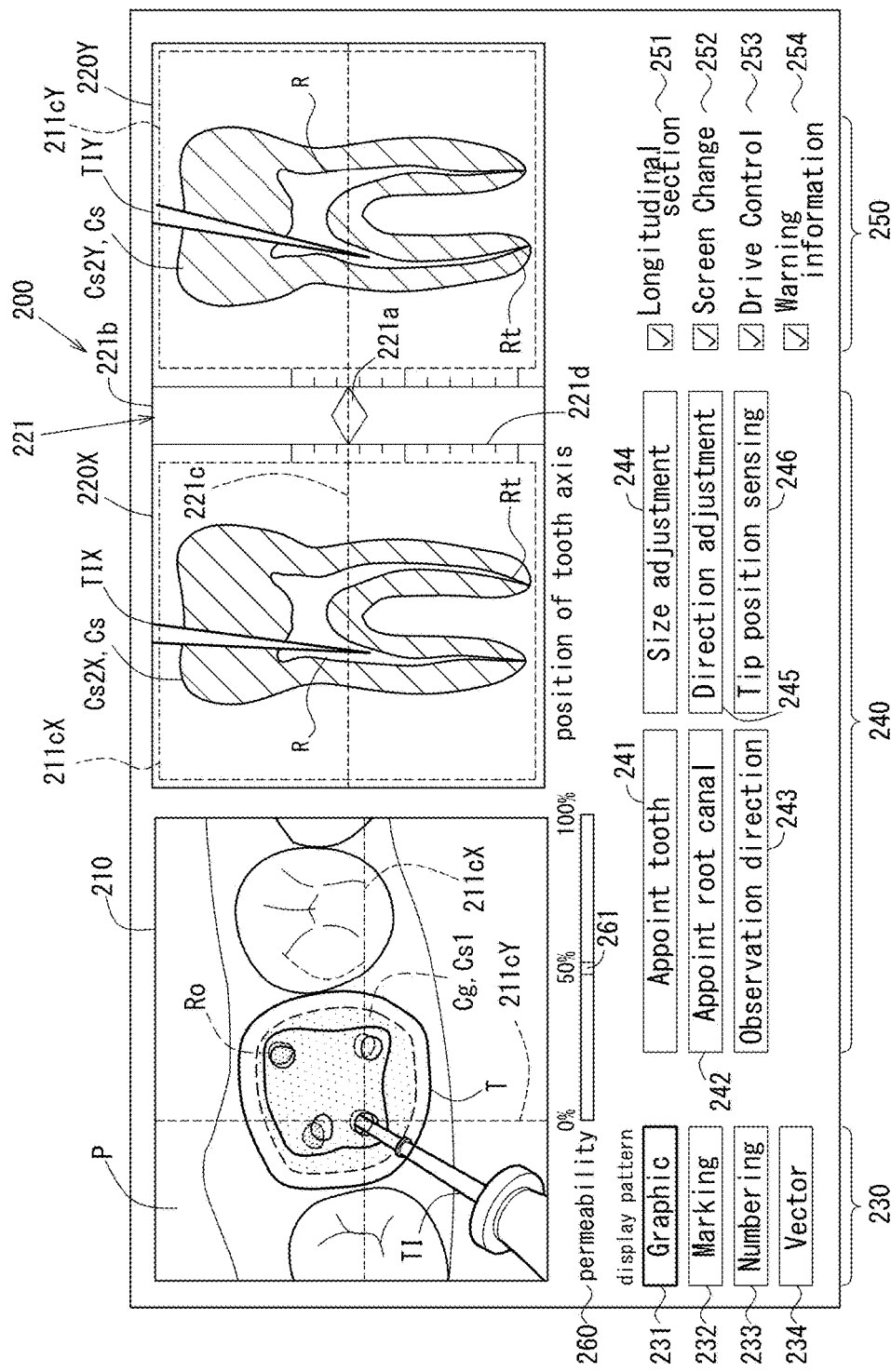
FIG. 24 shows an image overlapping display screen in still another display form.

FIG. 24 shows a modification of the image overlapping display screen 200 shown in FIG. 19.

The image overlapping display screen 200 shown in FIG. 24 includes a cross-sectional image display section 220 that displays a converted 2D cross-sectional image Cs2 as shown in FIG. 19 (in FIG. 24, shown as an "X direction cross-sectional image display section 220X that displays an "X direction converted 2D cross-sectional image Cs2X"), and also a Y direction cross-sectional image display section 220Y that displays a Y direction converted 2D cross-sectional image Cs2Y. The Y direction converted 2D cross-sectional image Cs2Y shows a cross-section of the tooth T as a target of display in a different direction.

The Y direction converted 2D cross-sectional image Cs2Y and the X direction converted 2D cross-sectional image Cs2X are both a two-dimensional cross-sectional image captured along the tooth axis direction, but are images along cross-sections perpendicular to each other.

The X direction cross-sectional image display section 220X displays an X direction tool image TIX as seen from the same line-of-sight direction as that of the X direction converted 2D cross-sectional image Cs2X. The Y direction cross-sectional image display section 220Y displays a Y direction tool image TIY as seen from the same line-of-sight direction as that of the Y direction converted 2D cross-sectional image Cs2Y.

Owing to such a structure, the root canal treating tool RTT, specifically, the position and the posture of the cutting tool 72, can be easily grasped three-dimensionally and visually.

A cross-section display line 211cX shown in the articulation face direction 2D image display section 210 shown in FIG. 24 specifies a cross-sectional position at which the X direction converted 2D cross-sectional image Cs2X is shown in the X direction cross-sectional image display section 220X. A cross-section display line 211cY shown in the articulation face direction 2D image display section 210 specifies a cross-sectional position at which the Y direction converted 2D cross-sectional image Cs2Y is shown in the Y direction cross-sectional image display section 220Y.

As shown in FIG. 24, the cross-section display line 211cX may also be displayed in the X direction cross-sectional image display section 220X as enclosing the X direction converted 2D cross-sectional image Cs2X, and the cross-section display line 211cY may also be displayed in the Y direction cross-sectional image display section 220Y as enclosing the Y direction converted 2D cross-sectional image Cs2Y. The cross-section display line 211cX and the cross-section display line 211cY may be displayed with different colors.

In the articulation face direction 2D image display section 210 in the state shown in FIG. 24, the cross-section display line 211cX may be moved upward and downward in articulation face direction 2D image display section 210 (in this example, toward the tongue and toward the cheek) by an operation on the mouse pointer to change the position of the cross-section at which the X direction converted 2D cross-sectional image Cs2X is shown in the X direction cross-sectional image display section 220X. The cross-section display line 211cY may be moved leftward and rightward in articulation face direction 2D image display section 210 (in this example, in the direction of the row of teeth) by an operation on the mouse pointer to change the position of the cross-section at which the Y direction converted 2D cross-sectional image Cs2Y is shown in the Y direction cross-sectional image display section 220Y.

The display position adjustment scroll bar 221 may be displayed in the X direction cross-sectional image display section 220X as a display position adjustment scroll bar 221X, and also in the Y direction cross-sectional image display section 220Y as a display position adjustment scroll bar 221Y. In this case, the display position adjustment scroll bars 221X and 221Y are controlled such that when one of the display position adjustment scroll bars 221X and 221Y is moved in the tooth axis direction, the other of the display position adjustment scroll bars 221X and 221Y is also moved by the same amount.

When the shaft TX of the root canal treating tool RTT advances deep into the root canal R, the shaft TX may occasionally be curved depending on the shape of the root canal R.

In this case, even if the three-dimensional shapes of the root canal treating tool RTT and the shaft TX are stored and the three-dimensional shape and the movement of the root canal treating tool RTT are detected, the three-dimensional shape and the movement of the shaft TX cannot be detected.

In order to avoid this, when the shaft TX is curved, the following control may be performed. When the shaft TX reaches a certain position inside the root canal R, X-ray image capturing is performed, and the postures of the X direction tool image TIX and the Y direction tool image TIY displayed in the X direction cross-sectional image display section 220X and the Y direction cross-sectional image display section 220Y are corrected in accordance with the current posture of the shaft TX.

The X-ray image capturing performed to correct the postures may be CT image capturing, or X-ray image capturing of emitting a plurality of X rays toward the subject at different angles to provide permeable images. In the latter case, it is preferable that the X rays are directed in the line-of-sight directions of the converted 2D cross-sectional images Cs2X and Cs2Y or directions opposite thereto.

The correction of the displayed posture may be performed as follows, for example. When an operation made by the operator of tracing the shaft TX on the X-ray image captured for the correction is accepted, the shape of the shaft TX is detected and the posture of the shaft TX is automatically corrected.

The correction of the posture may be performed a plurality of times along the advancement of the shaft TX into the root canal R. The actual position of the shaft TX in the root canal R may be detected so that the control section 20 notifies the next correction timing.

In the above-described example, the 2D captured image P captured by the X-ray CT image capturing device 40 is stored on the 2D image information storage section 32 of the storage device 30. In addition, the 2D captured image P is synthesized with the articulation face direction converted 2D image Cs1 based on the 3D information stored on the root canal measurement information storage section 33 to generate a synthesized image, and the synthesized image is displayed on the monitor 15. Alternatively, the articulation face direction converted 2D image Cs1 or the converted 2D cross-sectional image Cs2 may be displayed in a collimating screen of the microscope main body 50A of the microscope-inclusive dental care instrument 150 shown in FIG. 21.

The microscope-inclusive dental care instrument 150 includes the medical care chair 13 and a microscope unit 151 located to the side of the medical care chair 13. The microscope unit 151 includes a hanger arm 152 including a plurality of joints coupled to each other, the microscope main body 50A attached to a tip of the hanger arm 152, and a light support pillar 153 to which a base part of the hanger arm 152 is attached. The joints of the hanger arm 152 allows the microscope main body 50A to be located above a head rest of the medical care chair 13. Thus, the operator can observe the inside of the oral cavity of the surgical operation subject M1 (not shown in FIG. 21) lying supine on the medical care chair 13.

This will be described in more detail. The microscope main body 50A is a known microscope including an eye lens 50Aa, an object lens 50Ab, a focusing mechanism and the like. The operator directs the objective lens 50Ab toward the tooth T, which is a target of collimation, and looks into the eye lens 50Aa for collimation.

In this case, as shown in FIG. 20, the 2D image generation section 22 of the control section 20 and the 2D image information storage section 32 of the storage device 30, which are included in the medical care system 1 (see FIG. 1), are not needed.

In the above example, the articulation face direction converted 2D image Cs1 is displayed as overlapping the tooth T in the 2D captured image P in the articulation face direction 2D image display section 210 on the image overlapping display screen 200. Likewise, the articulation face direction converted 2D image Cs1 as described above is displayed as overlapping the tooth T in the 2D captured image P collimated by the microscope main body 50A on a screen seen through the eye lens 50Aa, and the converted 2D cross-sectional image Cs2 is displayed at a desired position on the screen.

As described above, according to the medical care system 1 acting as a display device, the 2D captured image P of the tooth T as the surgical operation target that is captured with visible light in an articulation face direction, and the articulation face direction converted 2D image Cs1 converted from the 3D information which is acquired on the tooth T and includes information on the root canal R inside the tooth T, are displayed in correspondence with each other on the monitor 15 or on the screen of the microscope main body 50A. Therefore, the root canal R inside the tooth T can be clearly shown on the 2D captured image P captured with visible light.

This will be described in more detail. The 2D captured image P of the tooth T as the surgical operation target that is captured with visible light in the articulation face direction, and the articulation face direction converted 2D image Cs1 converted from the 3D information which is acquired on the tooth T and includes information on the root canal R inside the tooth T, are displayed in correspondence with each other on the monitor 15 or on the screen of the microscope main body 50A. Therefore, the articulation face direction converted 2D image Cs1, which displays the 3D information two-dimensionally, can show, for example, the position or size of the root canal orifice Ro or whether the tooth T has been treated before or not. The articulation face direction converted 2D image Cs1 can clearly show the root canal orifice Ro inside the tooth T, on the 2D captured image P of a surface of the tooth T that is captured with visible light. Therefore, the operator can perform an accurate surgical operation while checking the 2D captured image P showing the surface of the tooth T and also grasping the position, size or direction of the root canal R inside the tooth T.

The converted 2D image adjustment operation section 11e is provided to adjust the articulation face direction converted 2D image Cs1, which is of a cross-section parallel to the articulation face direction, so as to be accommodated to the 2D captured image P. Owing to this, the articulation face direction converted 2D image Cs1 is adjusted to be comparable with the 2D captured image P. Thus, an accurate position of the root canal orifice Ro can be grasped.

The converted 2D permeable image Cg of the articulation face direction converted 2D image Cs1 may be displayed in an overlapping manner. Therefore, the 2D captured image P and the converted 2D permeable image Cg can be easily compared with each other. Thus, the position, size or direction of the root canal orifice Ro with respect to the tooth T in the 2D captured image P can be shown more accurately.

In the converted 2D marking image Cm, the position of root canal orifice Ro is represented by "x". Owing to this, the position, size or direction of the root canal orifice Ro can be perceived intuitively.

The articulation face direction converted 2D image Cs1 and the 2D captured image P adjusted by the converted 2D image adjustment operation section 11e to be accommodated to each other may be displayed on the same monitor 15 in a switched manner by the operation of stepping on the foot controller 14. Therefore, the 2D captured image P and the articulation face direction converted 2D image Cs1 can be each displayed clearly. Thus, the operator can grasp the position, size or direction of the root canal orifice Ro with respect to the tooth T in the 2D captured image P.

The display position in the tooth axis direction can be adjusted by use of the display position adjustment scroll bar 221. Therefore, the articulation face direction converted 2D image Cs1 at the adjusted display position in the tooth axis direction can be displayed. Thus, during the root canal treatment, the position of the tip of the surgical operation tool 70, and the direction or size of the root canal orifice Ro, can be continuously displayed while being changed along the tooth axis direction. The operator can correctly grasp the direction or size of the root canal R in the tooth axis direction while checking the 2D captured image P.

The 3D information storage section 31 that stores 3D information and the converted 2D image generation section 21 that generates the articulation face direction converted 2D image Cs1 based on the 3D information stored on the 3D information storage section 31 are provided. Owing to this, the 3D information acquired by the X-ray CT image capturing device 40 is stored on the 3D information storage section 31, and the 3D information stored on the 3D information storage section 31 is read so that the converted 2D image generation section 21 generates the articulation face direction converted 2D image Cs1. The generated articulation face direction converted 2D image Cs1 is displayed.

The target tooth specification operation section 11b specifies a tooth T which is a surgical operation target from the 2D captured image P. The control section 20 extracts the 3D information corresponding to the tooth T specified by the target tooth specification operation section 11b, among the 3D information stored on the 3D information storage section 31. Owing to these elements, the tooth T which is a surgical operation target is specified by the target tooth specification operation section 11b from the 2D captured image P showing a plurality of teeth T and the gum, and the 3D information on the specified tooth T is extracted. The articulation face direction converted 2D image Cs1 based on the 3D information on the tooth T is displayed. Therefore, even when the 2D captured image P shows elements other than the surgical operation target, the articulation face direction converted 2D image Cs1 of the tooth T as the surgical operation target can be displayed with certainty.

The 2D image information storage section 32 is provided to store the 2D captured image P. Owing to this, the 2D captured image P stored on the 2D image information storage section 32 is read and displayed as the articulation face direction converted 2D image Cs1. Therefore, the 2D captured image P captured by the intraoral camera 50 can be displayed on the monitor 15, which is a display device different from the intraoral camera 50. For displaying articulation face direction converted 2D image Cs1 directly on the screen of the microscope main body 50A for collimation in an overlapping manner, neither the 2D image information storage section 32 nor the 2D image generation section 22 is needed.

The converted 2D cross-sectional image Cs2 at a cross-section in the tooth axis direction may be displayed in the cross-sectional image display section 220, while the 2D captured image P may be displayed in the articulation face direction 2D image display section 210. Owing to this, during the root canal treatment, the position of the tip of the surgical operation tool 70 can be checked with the converted 2D cross-sectional image Cs2 at a cross-section in the tooth axis direction during the root canal treatment.

The converted 2D cross-sectional image Cs2 at a cross-section in the tooth axis direction may be displayed in the cross-sectional image display section 220, while the articulation face direction converted 2D image Cs1 at a cross-section parallel to the articulation face direction may be displayed in the articulation face direction 2D image display section 210. Owing to this, the articulation face direction converted 2D image Cs1 at a cross-section parallel to the articulation face direction, which is generated based on the 3D information, the converted 2D cross-sectional image Cs2 at a cross-section in the tooth axis direction, and the 2D captured image P can be displayed concurrently and compared with one another.

In the cross-sectional image display section 220, the converted 2D cross-sectional image Cs2 at a cross-section in the tooth axis direction, and the scale 221d which shows a distance from the root apex Rt to the crown, may be displayed. Owing to this, the distance to the root apex Rt can be checked.

The medical care system 1 includes the surgical operation tool 70 (70a, 70b) usable to perform a surgical operation on the tooth T. Therefore, the operator can perform an accurate surgical operation by use of the surgical operation tool 70 (70a, 70b) while checking the articulation face direction converted 2D image Cs1 and the 2D captured image P displayed on the medical care system 1 acting as a display device.

The tip position detection section 24 is provided to detect the position of the tip of the surgical operation tool 70 (70a, 70b) in the tooth T, and the articulation face direction converted 2D image Cs1 at the position of the tip of the surgical operation tool 70 (70a, 70b) is displayed in the articulation face direction 2D image display section 210. Therefore, the surgical operation can be performed more accurately and safely.

When the tip of the surgical operation tool 70, detected by the root canal length measurement device 60 that detects the length of the root canal R, the root canal measurement information storage section 33 that stores the root canal length information detected by the root canal length measurement device 60, and the tip position detection section 24, has approached the root apex Rt, namely, is at a position away from the root apex Rt by, for example, a few millimeters, the notification section 16 makes a notification of this state.

Therefore, the operator can recognize that the tip has approached the root apex Rt and thus can perform the surgical operation carefully and cautiously so that the tip does not reach the root apex Rt.

The surgical operation tool driving control section 25 controls the driving of the surgical operation tool 70 when the surgical operation tool 70 is at a position away from the root apex Rt by a few millimeters. Therefore, the surgical operation tool 70 is prevented from touching the root apex Rt, which would be cause a damage on the root canal, and thus the surgical operation can be performed safely.

The position of the elements at which the notification section 16 or the surgical operation tool driving control section 25 are to be actuated, namely, the distance (millimeters) between the elements and the root apex Rt at which the notification section 16 or the surgical operation tool driving control section 25 are to be actuated, may be freely set in accordance with the preference of the operator.

The tip deviation detection section 28 is provided to detect that the tip of the surgical operation tool 70 (70a, 70b) has deviated from a predetermined root canal R. Owing to this, even when the route of the sub root canal or the like is complicated, the surgical operation can be performed safely.

The driving of the surgical operation tool 70 (70a, 70b) is controlled or notified based on that the tip deviation detection section 28 has detected the deviation of the tip of the surgical operation tool 70 (70a, 70b). Therefore, even when the route of the root canal R is complicated, the surgical operation can be performed accurately along a predetermined route. The notification may be made in the form of voice, buzzer, melody, vibration, lighting of an LED or the like, blinking of light or the like.

The driving load detection section 29 is provided to detect the rotation torque or vibration output of the surgical operation tool 70 (70a, 70b), and the surgical operation tool driving control section 25 is provided to control the driving of the surgical operation tool 70 (70a, 70b) when the output detected by the driving load detection section 29 reaches a pre-stored value output value. Owing to these elements, the surgical operation tool 70 (70a, 70b) is prevented from being broken due to excessive load, and thus the surgical operation can be performed safely.

The two-dimensional captured image in the present invention corresponds to the 2D captured image P in the above-described embodiment; and similarly, the three-dimensional information corresponds to the 3D information;

two-dimensional display information corresponds to the articulation face direction converted 2D image Cs1;

the display section corresponds to the monitor 15;

the dental image display device corresponds to the medical care system 1 acting as the display device;

the adjustment section corresponds to the converted 2D image adjustment operation section 11e;

the marking corresponds to step s7 in which the converted 2D marking image Cm is generated;

the two-dimensional display information corresponds to the converted 2D permeable image Cg;

the tooth axis direction display position adjustment section corresponds to the display position adjustment scroll bar 221;

the three-dimensional information storage section corresponds to the 3D information storage section 31;

the two-dimensional display information generation section corresponds to the converted 2D image generation section 21;

the tooth specification section corresponds to the target tooth specification operation section 11b;

the corresponding information extraction section corresponds to the control section 20;

the two-dimensional captured image storage section corresponds to the 2D image information storage section 32;

the two-dimensional cross-section display information corresponds to the converted 2D cross-sectional image Cs2;

the scale corresponds to the scale 221d;

the surgical operation tool corresponds to the surgical operation tool 70, the root canal treating hand piece 70a and the file 70b;

the dental surgical operation device corresponds to the medical care system 1;

the detection section corresponds to the tip position detection section 24;

the root canal length measurement device corresponds to the root canal length measurement device 60;

the root canal length information storage section corresponds to the root canal measurement information storage section 33;

the operation section corresponds to the notification section 16 and the surgical operation tool driving control section 25;

the notification section and the deviation detection section correspond to the notification section 16;

the driving control section corresponds to the surgical operation tool driving control section 25;

the route deviation detection section corresponds to the tip deviation detection section 28; and the output detection section corresponds to the driving load detection section 29.

However, the present invention is not limited to the structure of the above-described embodiment, and may be carried out in any of various other embodiments.

For example, the line-of-sight direction specification operation section 11a specifies the line-of-sight direction of the 2D captured image P captured by the intraoral camera 50. Alternatively, the intraoral camera 50 or the microscope main body 50A may be equipped with a posture detection sensor, so that the line-of-sight direction of the 2D captured image P can be set based on the detection result of the posture detection sensor.

The converted 2D cross-sectional image Cs2, which is a cross-sectional view of the tooth T, is displayed in the cross-sectional image display section 220. Alternatively, a side view of the tooth T may be displayed. Still alternatively, only the 2D captured image P may be displayed, namely, the articulation face direction converted 2D image Cs1 may not be displayed, in the articulation face direction 2D image display section 210, and the converted 2D cross-sectional image Cs2 may be displayed in the cross-sectional image display section 220.

In the above embodiment, the 3D information is acquired by the X-ray CT image capturing device 40. Alternatively, the 3D information may be acquired by an MRI image capturing device or an optical coherence tomography (OCT) image capturing device. The device for capturing a two-dimensional image with visible light may be an intraoral camera, a microscope, an endoscope, or an optical camera.

The size or direction of the articulation face direction converted 2D image Cs1 is adjusted so as to be accommodated to the 2D captured image P. Oppositely, the size or direction of the 2D captured image P may be adjusted so as to be accommodated to the articulation face direction converted 2D image Cs1. Alternatively, both of the articulation face direction converted 2D image Cs1 and the 2D captured image P may be adjusted to be accommodated to each other.

The articulation face direction converted 2D image Cs1 may be displayed in a manner in which the operator can easily grasp the root canal R. For example, the converted 2D permeable image Cg showing the root canal orifices Ro and the converted 2D numbering image Cn showing the numbers of the root canal orifices Ro may be displayed together. The converted 2D marking image Cm representing the positions of the root canal orifices Ro by "x" and the converted 2D numbering image Cn showing the numbers of the root canal orifices Ro may be displayed together. The converted 2D arrow image Cv representing the directions of the root canals R by arrows and the converted 2D numbering image Cn showing the numbers of the root canal orifices Ro may be displayed together.

In the converted 2D permeable image Cg, the root canal orifices Ro may be colored, and only the root canal orifices Ro in the colored state may be displayed as overlapping the 2D captured image P. Alternatively, in the converted 2D permeable image Cg, the profile of the tooth T or the root canal orifices Ro may be emphasized, and the tooth T or the root canal orifices Ro in such a state may be displayed as overlapping the 2D captured image P.

DESCRIPTION OF THE REFERENCE NUMERALS

1 . . . Medical care system
11b . . . Target tooth specification operation section
11e . . . Converted 2D image adjustment operation section
15 . . . Monitor
16 . . . Notification section
20 . . . Control section
21 . . . Converted 2D image generation section
24 . . . Tip position detection section
25 . . . Surgical operation tool driving control section
28 . . . Tip deviation detection section
29 . . . Driving load detection section
31 . . . 3D information storage section
32 . . . 2D image information storage section
33 . . . Root canal measurement information storage section
60 . . . Root canal length measurement device
70 . . . Surgical operation tool
70a . . . Root canal treating hand piece
70b . . . File
221 . . . Display position adjustment scroll bar
221d . . . Scale
Cg . . . Converted 2D permeable image
Cm . . . Converted 2D marking image
Cs1 . . . Articulation face direction converted 2D image
Cs2 . . . Converted 2D cross-sectional image
P . . . 2D captured image
R . . . Root canal
Ro . . . Root canal orifice
Rt . . . Root apex
T . . . Tooth

What is claimed is:

1. A medical care system comprising:
a camera configured to capture a two dimensional captured image of one or more teeth in a direction of an occlusal surface by visible light;
a control computer comprising a display, a storage, and a controller,
wherein the display is configured to display the two dimensional captured image;
wherein the storage is configured to store three-dimensional information of the one or more teeth, wherein the three-dimensional information is acquired by an X-ray CT image capturing device; and
wherein the controller is connected to the camera, the X-ray CT image capturing device, the display, and the storage, and
wherein the controller comprises a processor configured to, upon execution of software stored in the storage and executable on the processor, perform:
causing the display to display the two-dimensional captured image;
controlling specifying of a tooth that is a target of interest from the displayed two-dimensional captured image and the X-ray CT image capturing device, by accepting input by a pointing device selecting an appoint tooth selection icon, and specifying the tooth that is the target of interest from the two-dimensional captured image showing a plurality of teeth and gums;
specifying a line-of-sight direction of the camera and the X-ray CT image capturing device to be in a planar direction crossing a tooth axis of the specified tooth, wherein the planar direction is an articulation face crossing the tooth axis at an angle within a range of ±30 degrees off the tooth axis;
extracting three-dimensional information corresponding to the specified tooth from the three-dimensional information stored in the storage along the planar direction crossing the tooth axis of the specified tooth;
generating two-dimensional display information based on the extracted three-dimensional information; and
controlling display of the two-dimensional captured image captured by the camera of the visible light from along the line-of-sight direction of the camera and the two-dimensional display information in correspondence with the planar direction crossing the tooth axis of the specified tooth in an overlapping manner on the display,
wherein the two-dimensional display information results from translating the three-dimensional information on the specified tooth to two dimensions along a predetermined plane that is parallel to the direction of the occlusal surface,
wherein the three-dimensional information contains information on a root canal inside the specified tooth,
wherein, by displaying the two-dimensional display information and the two-dimensional captured image in an overlapping manner on the display allows the root canal inside the specified tooth to be viewed together with the captured image of the specified tooth.

2. The medical care system according to claim 1,
the controller controlling display of, as part of the information on the root canal inside the specified tooth, information on a root canal site and/or a root canal orifice, and
the controller causing the display to display the root canal site and/or the root canal orifice being colored or marked.

3. The medical care system according to claim 1,
the controller causing the display to display a permeability adjustment scroll bar together with the two-dimensional captured image, and
in response to an operation on the permeability adjustment scroll bar, the controller adjusting a permeability of the displayed two-dimensional captured image such that each of the two-dimensional display information and the two-dimensional captured image is visually recognizable.

4. The medical care system according to claim 1, the two-dimensional display information and the two-dimensional captured image being displayed in a switched manner or concurrently side by side on the display.

5. The medical care system according to claim 1, the two-dimensional display information being two-dimensional image display information obtained as a result of forming the two-dimensional display information into an image.

6. The medical care system according to claim 1,
the controller causing the display to display an adjustment scroll bar, and
in response to an operation on the adjustment scroll bar, the controller adjusting a position of the predetermined plane in a tooth axis direction that is perpendicular to the direction of the occlusal surface.

7. The medical care system according to claim 1,
the storage configured to store the two-dimensional captured image.

8. The medical care system according to claim 1,
the predetermined plane being a cross-section in a tooth axis direction along a tooth axis of the tooth; and
the two-dimensional display information being two-dimensional cross-section display information along the cross-section in the tooth axis direction, and being displayed concurrently with the two-dimensional captured image.

9. The medical care system according to claim 8, the two-dimensional cross-section display information and the two-dimensional display information along a plane parallel to the occlusal surface being displayed concurrently.

10. The medical care system according to claim 9, the two-dimensional cross-section display information in the tooth axis direction being displayed together with a scale that displays a distance from a root apex to a tooth crown.

11. A dental surgical operation device, comprising:
the medical care system according to claim 1; and
a surgical operation tool usable to perform a surgical operation on the tooth and connected to the controller of the medical care system.

12. The dental surgical operation device according to claim 11,
the surgical operation tool comprising a sensor to detect a position of a tip of the surgical operation tool in the tooth, and
the controller controlling the display of the two-dimensional display information so that the predetermined plane is a plane at a position corresponding to the position of the detected tip.

13. The dental surgical operation device according to claim 12, further comprising:
a root canal length measurement device that detects a root canal length and that is connected to the controller;
the storage storing root canal length information on the detected root canal length.

14. The dental surgical operation device according to claim 13, further comprising a notification section that notifies that the position of the tip is at the predetermined position with respect to the root canal length information.

15. The dental surgical operation device according to claim 13, the controller controlling driving of the surgical operation device depending on the position of the detected tip.

16. The dental surgical operation device according to claim 11,
the surgical operation tool comprising a sensor that detects a position of a tip of the surgical operation tool,
the storage storing root canal route information on a route of the root canal based on the three-dimensional information,
the controller configured to detect that the detected position of the tip of the surgical operation tool has deviated from the stored route of the root canal.

17. The dental surgical operation device according to claim 16, the controller configured to control the driving of the surgical operation tool based on the detection of the deviation of the tip of the surgical operation tool.

18. The dental surgical operation device according to claim 16, further comprising a deviation notification section that performs a notification based on the detection of the deviation of the tip of the surgical operation tool.

19. The dental surgical operation device according to claim 11,
the controller configured to:
detect a rotation torque or a vibration output of the surgical operation tool, and
control the driving of the surgical operation tool when the detected rotation torque or the detected vibration output reaches a value stored in advance.

20. A dental image display method executed by a medical care system, comprising:
capturing, by a camera, a two dimensional captured image of one or more teeth in a direction of an occlusal surface by visible light;
storing three-dimensional information of one or more teeth in a storage of a control computer of the medical care system, wherein the three-dimensional information is acquired by an X-ray CT image capturing device;
displaying, by a display of the control computer, the two-dimensional captured image;
controlling, by a controller of the control computer connected thereof, the camera, the storage, the X-ray CT image capturing device, and the display, upon execution of software stored in the storage and executable on a processor of the controller for:
specifying of a tooth that is a target of interest from the displayed two-dimensional captured image and the X-ray CT image capturing device by accepting input by a pointing device selecting an appoint tooth selection icon, and specifying the tooth that is the target of interest from the two-dimensional captured image showing a plurality of teeth and gums;
specifying a line-of-sight direction of the camera and the X-ray CT image capturing device to be in a planar direction crossing a tooth axis of the specified tooth, wherein the planar direction is an articulation face crossing the tooth axis at an angle within a range of ±30 degrees off the tooth axis;

extracting, by the controller, three-dimensional information corresponding to the specified tooth from the three-dimensional information stored in the storage along the planar direction crossing the tooth axis of the specified tooth;

generating, by the controller, two-dimensional display information based on the extracted three-dimensional information; and controlling, by the controller, display of the two-dimensional captured image captured by the camera of the visible light from along the line-of-sight direction of the camera and the two-dimensional display information in correspondence with the planar direction crossing the tooth axis of the specified tooth in an overlapping manner on a display of the medical care system, the two-dimensional display information resulting from translating the three-dimensional information on the specified tooth to two dimensions along a predetermined plane that is parallel to the direction of the occlusal surface, the three-dimensional information containing information on a root canal inside the specified tooth, and displaying the two-dimensional display information and the two-dimensional captured image in an overlapping manner on the display to allow the root canal inside the specified tooth to be viewed together with the captured image of the specified tooth.

* * * * *

UNITED STATES PATENT AND TRADEMARK OFFICE
CERTIFICATE OF CORRECTION

| | |
|---|---|
| PATENT NO. | : 10,204,443 B2 |
| APPLICATION NO. | : 14/199680 |
| DATED | : February 12, 2019 |
| INVENTOR(S) | : Fleer et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 190 days.

Signed and Sealed this
Seventh Day of April, 2020

Andrei Iancu
*Director of the United States Patent and Trademark Office*